(12) United States Patent
Flygare et al.

(10) Patent No.: US 11,471,446 B2
(45) Date of Patent: Oct. 18, 2022

(54) COMPOUNDS FOR TREATMENT OF HYPOPROLIFERATIVE DISORDERS

(71) Applicant: LU LICENSE AB, Lund (SE)

(72) Inventors: Johan Flygare, Lund (SE); Lars Johansson, Bromma (SE); Thomas Lundbäck, Kullavik (SE)

(73) Assignee: LU LICENSE AB, Lund (SE)

( * ) Notice: Subject to any disclaimer, the term of this patent is extended or adjusted under 35 U.S.C. 154(b) by 101 days.

(21) Appl. No.: 15/772,633

(22) PCT Filed: Nov. 3, 2016

(86) PCT No.: PCT/EP2016/076550
§ 371 (c)(1),
(2) Date: May 1, 2018

(87) PCT Pub. No.: WO2017/076968
PCT Pub. Date: May 11, 2017

(65) Prior Publication Data
US 2019/0111034 A1  Apr. 18, 2019

(30) Foreign Application Priority Data
Nov. 3, 2015  (SE) .................................. 1551419-3

(51) Int. Cl.
| | | |
|---|---|---|
| *A61K 31/4365* | (2006.01) | |
| *A61K 31/444* | (2006.01) | |
| *A61K 31/496* | (2006.01) | |
| *A61K 31/517* | (2006.01) | |
| *A61K 31/551* | (2006.01) | |
| *A61P 7/06* | (2006.01) | |
| *A61P 19/10* | (2006.01) | |

(52) U.S. Cl.
CPC ........ *A61K 31/4365* (2013.01); *A61K 31/444* (2013.01); *A61K 31/496* (2013.01); *A61K 31/517* (2013.01); *A61K 31/551* (2013.01); *A61P 7/06* (2018.01)

(58) Field of Classification Search
CPC .............. A61K 31/4365; A61K 31/444; A61K 31/496; A61K 31/517; A61K 31/551; A61P 7/06; A61P 19/10; A61P 21/06; C12Y 207/11022
See application file for complete search history.

(56) References Cited

U.S. PATENT DOCUMENTS

| 8,598,344 B2 | 12/2013 | Porter et al. |
| 9,321,737 B2 | 4/2016 | Roninson et al. |
| 2007/0219234 A1 | 9/2007 | Oizumi |

FOREIGN PATENT DOCUMENTS

| WO | WO WO 03103661 A1 | 12/2003 |
| WO | WO 2013/040153 A1 | 3/2013 |
| WO | WO 2013/116786 | 8/2013 |
| WO | WO 2013/138101 A2 | 9/2013 |
| WO | WO 2014/029726 | 2/2014 |
| WO | WO 2014/072435 A1 | 5/2014 |
| WO | WO 2014/090692 | 6/2014 |
| WO | WO 2014/106606 | 7/2014 |
| WO | WO 2014/154723 | 10/2014 |
| WO | WO 2014/194201 A2 | 12/2014 |
| WO | WO 2015/144290 A1 | 10/2015 |
| WO | WO 2015/144290 A8 | 10/2015 |

OTHER PUBLICATIONS

Jaako (Disruption of the 5S RNP—Mdm2 interaction significantly improves the erythroid defect in a mouse model for Diamond-Blackfan anemia, Leukemia. Nov. 2015 ; 29(11): 2221-2229).*
Donner (CDK8 is a Stimulus-Specific Positive Coregulator of p53 Target Genes, Mol Cell. Jul. 6, 2007; 27(1): 121-133).*
Akiyama et al. 2005 "Successful Treatment of Diamond-Blackfan Anemia With Metoclopramide" American Journal of Hematology 78:295-298.
Dale, Trevor, et.al., "A selective chemical probe for expoloring the role of CDK8 and CDK19 in human disease", Nature Chemical Biology, vol. 11, Dec. 2015, 973-983.
Dror, Y. et al. Draft consensus guidelines for diagnosis and treatment of Shwachman-Diamond syndrome, Ann N Y Acad Sci. 2011, 1242:40-55.
Flygare, J. et al. Diamond-Blackfan anemia: erythropoiesis lost in translation, Blood. 2007;109(8):3152-4.
Fumagalli, Stefano, et.al., "The Role of p53 in Ribosomopathies", Seminars in Hematology, vol. 48. No. 2, Apr. 2011, pp. 97-105.
Jaako et al. Mice with ribosomal protein S19 deficiency develop bone marrow failure and symptoms like patients with Diamond-Blackfan anemia, Blood. 2011;118(23):6087-96.
Mallinger, Aurélia, et.al., "Discovery of Potent, Selective, and Orally Bioavailable Small-Molecule Modulators of the Mediator Complex-Associated Kinases CDK8 and CDK19", J.Med.Chem, 2016, 59, 1078-1101.
Niles, A.L. et al., In Vitro Viability and Cytotoxicity Testing and Same-Well Multi-Parametric Combinations for High Throughput Screening, Curr Chem Genomics. 2009, 3, 33-41.
Porter et al. Cyclin-dependent kinase 8 mediates chemotherapy-induced tumor-promoting paracrine activities, Natl. Acad. Sci. Proc. 2012, 109, 13799-13804.
Saito, K. et al. Discovery and structure-activity relationship of thienopyridine derivatives as bone anabolic agents, Bioorg. Med. Chem. 2013, 21, 1628-42.
Siva et al. A Robust Assay For Diamond Blackfan Anemia Candidate Drugs, 55th ASH annual meeting, New Orleans, LA, Dec. 7-10, 2013; Abstract # 2472.

(Continued)

*Primary Examiner* — Theodore R. Howell
(74) *Attorney, Agent, or Firm* — Sterne, Kessler, Goldstein & Fox, P.L.L.C.

(57) ABSTRACT

The present invention relates to the use of CDK8 and/or CDK19 inhibitors in the treatment of ribosomopathies as well as conditions characterized by reduced number of hematopoietic stem cells and/or progenitor cells; and bone anabolic disorders.

20 Claims, 21 Drawing Sheets

(56) References Cited

OTHER PUBLICATIONS

Vlachos, A. et al. How I treat Diamond-Blackfan anemia, Blood. 2010;116(19):3715-23.

Wei, S. et al., "Lenalidomide promotes p53 degradation by inhibiting MDM2 auto-ubiquitination in myelodysplastic syndrome with chromosome 5q deletion", Oncogene (2013), 32, 1110-1120.

* cited by examiner

| DiscoverX Kinome Scan ||
|---|---|
| Compound name --> | DBA-4 |
| DiscoveRx Gene Symbol | %cntrl @ 10000 nM |
| CDK11 (CDK19) | 0 |
| CSNK1A1 | 11 |
| CSNK1A1L | 25 |
| CSNK1D | 10 |
| CSNK1E | 14 |
| CSNK1G1 | 84 |
| CSNK1G2 | 73 |
| CSNK1G3 | 67 |
| DAPK1 | 84 |
| DYRK1A | 50 |
| DYRK1B | 41 |
| DYRK2 | 46 |
| GCN2(Kin.Dom.2,S808G) | 94 |
| HIPK1 | 61 |
| p38-alpha | 88 |
| PIM1 | 87 |
| RSK4(Kin.Dom.2-C-terminal) | 72 |
| TGFBR1 | 95 |

Fig. 4

DBA-10

Healthy donor

DBA Patient (RPS35a mutation)

Glycophorin A (CD235a)

DBA-7

COMPOUNDS FOR TREATMENT OF HYPOPROLIFERATIVE DISORDERS

CROSS-REFERENCE TO RELATED APPLICATIONS

This application is the National Stage of International Patent Application No. PCT/EP2016/076550, filed Nov. 3 2016, which claims the benefit of Swedish application number 1551419-3, filed Nov. 3, 2015, the disclosures of which are incorporated herein by reference in their entireties.

FIELD OF INVENTION

The present invention relates to the field of treatment of ribosomopathies, and conditions characterized by reduced number of hematopoietic stem cells and/or progenitor cells. The invention also relates to treatment of disorders that can be improved by increasing bone formation. The invention discloses that CDK8 and/or CDK19 inhibitors may be useful in treatment of such disorders.

BACKGROUND OF INVENTION

Diamond-Blackfan Anemia (DBA) can be considered as a ribosomopathy model indication. It is caused by mono-allelic inactivating mutations in ribosomal protein genes causing disturbed ribosome biogenesis. DBA is a pure red blood cell aplasia, characterized by severely decreased numbers of erythropoietin-responsive red blood cell precursors. DBA Patients are currently treated with blood transfusions or corticosteroids, therapies that are associated with severe adverse effects and treatment-related death (Blood. 2010 Nov. 11; 116(19):3715-23). Shwachman-Diamond Syndrome (SDS) is an example of another ribosomopathy caused by bi-allelic hypomorphic mutations in the SBDS gene that leads to disturbed maturation of the large ribosomal subunit (Ann N Y Acad Sci. 2011 December 1242: 40-55). DBA and SDS are merely two out of several other "Ribosomopathies" caused by failed ribosome biogenesis. The mechanisms behind the symptoms such as bone marrow failure in these syndromes are poorly understood but are likely related to consequences of dysregulation of mRNA translation and/or failure in ribosome biogenesis which may induce activation of stress responses. Treatment options are limited for these diseases and new mechanism-based therapies are needed.

SUMMARY OF INVENTION

The present inventors have discovered that the enzymes cyclin-dependent kinase 8 (CDK8) and cyclin-dependent kinase 19 (CDK19) play a key role in the etiology of ribosomopathies and disorders characterized by reduced number of hematopoietic stem cells and/or progenitor cells, as well as in bone anabolic disorders.

Thus in a main aspect the present invention concerns a compound for use in the treatment of an indication selected from the group consisting of ribosomopathy; a disease characterized by reduced number of hematopoietic stem cells and/or progenitor cells; and bone anabolic disorders wherein the compound is an inhibitor of cyclin-dependent kinase 8 (CDK8) and/or cyclin-dependent kinase 19 (CDK19).

This figure demonstrates that DBA-1 confers a partial dose-dependent rescue of proliferation in RPS19-deficient murine erythroid progenitor cells. Cells were cultured and analysed as described in Example 1.

Figure 2:
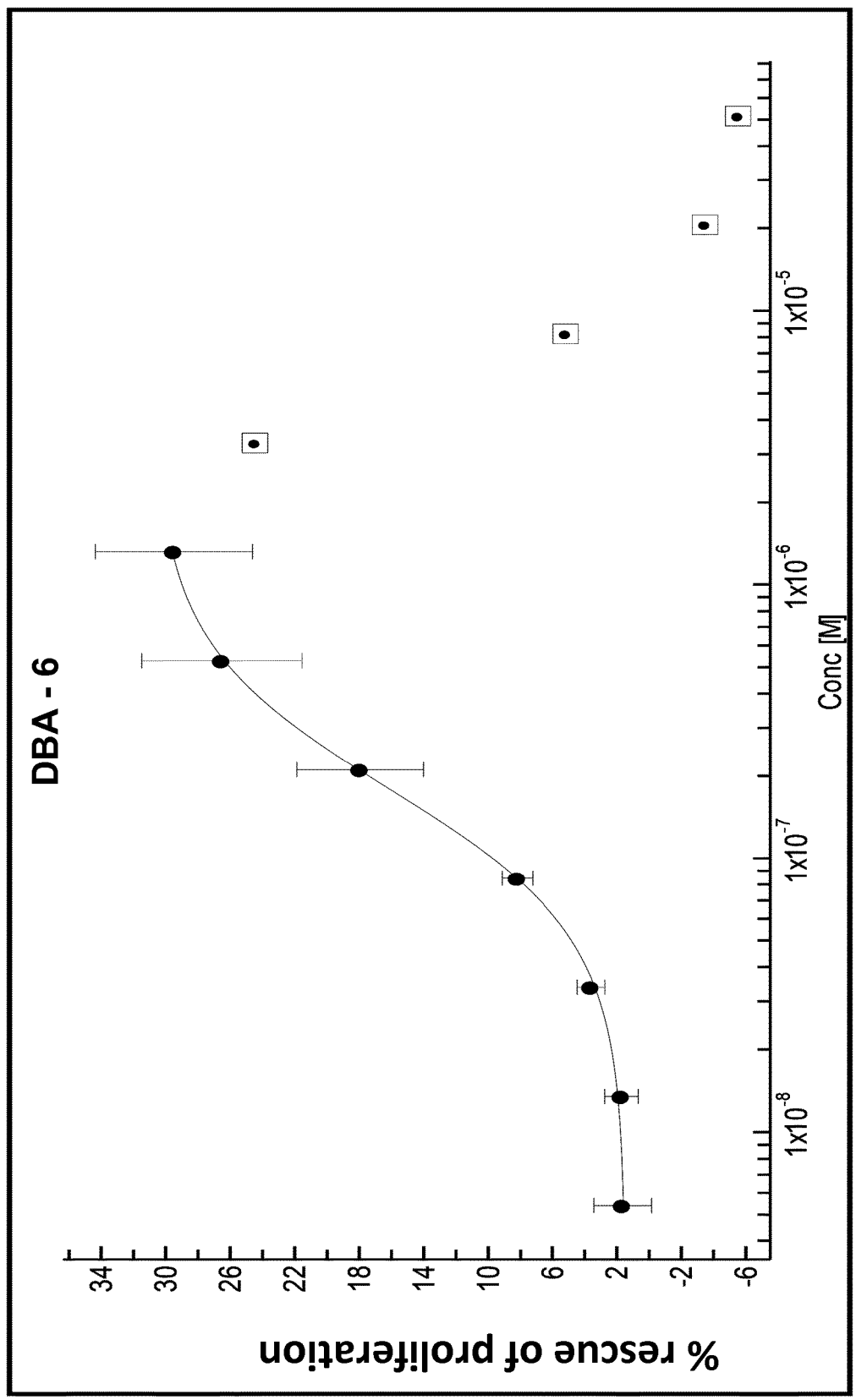

FIG. 2: DBA-6 confers a dose-dependent rescue of proliferation of RPS19-deficient murine erythroid progenitor cells.

This figure demonstrates that the DBA-1 analogue DBA-6 confers a partial dose-dependent rescue of proliferation in RPS19-deficient murine erythroid progenitor cells.

Figure 3:
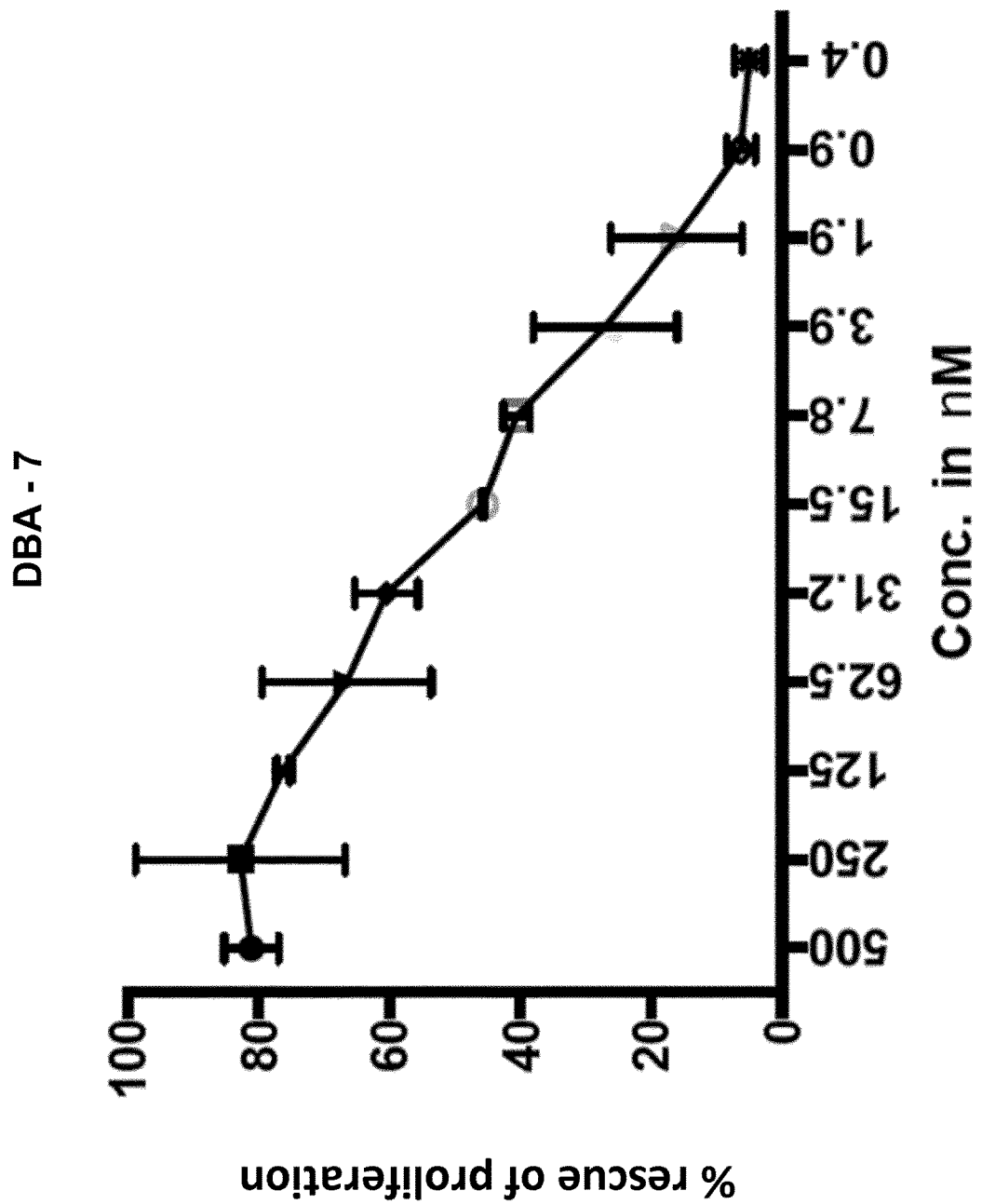

FIG. 3: DBA-7 confers dose-dependent rescue of proliferation of RPS19-deficient murine erythroid progenitor cells.

This figure demonstrates that the DBA-1 and DBA-6 analogue DBA-7 (15w in Saito et al. Bioorg. Med. Chem. 2013, 21, 1628-42) confers a partial dose-dependent rescue of proliferation in RPS19-deficient murine erythroid progenitor cells.

FIG. 4: DBA-4 is a CDK19 inhibitor.

DBA-4 was tested on 18 selected kinases by DiscoveRx LeadHunter™ Discovery Services.

Figure 5:
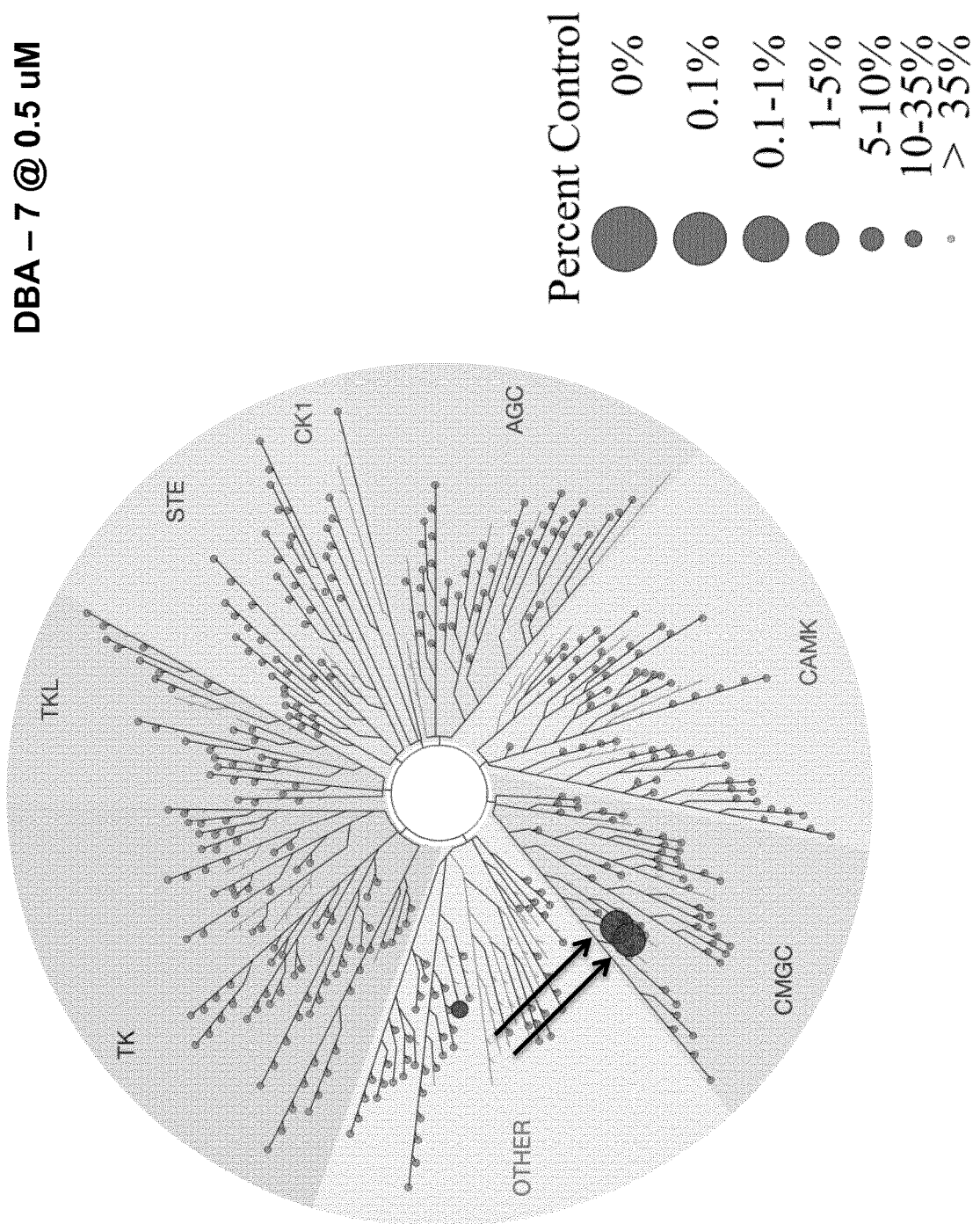

FIG. 5: Interaction Map from DiscoveRx KinomeScan testing the DBA-7 (0.5 uM) on 468 kinases.

The figure shows an artistic representation (TREEspot™) of the human kinome phylogenetic tree. At 0.5 uM DBA-7 is a specific CDK8/CDK19 inhibitor. Arrows point at CDK8 and CDK19. The results are similar to 2 uM DBA-9 published in patent application no. US 2014/0038958 and in Porter et al. J Biomol Screen. 1999; 4(2):67-73. and patent WO 2013116786 A1.

Figure 6:
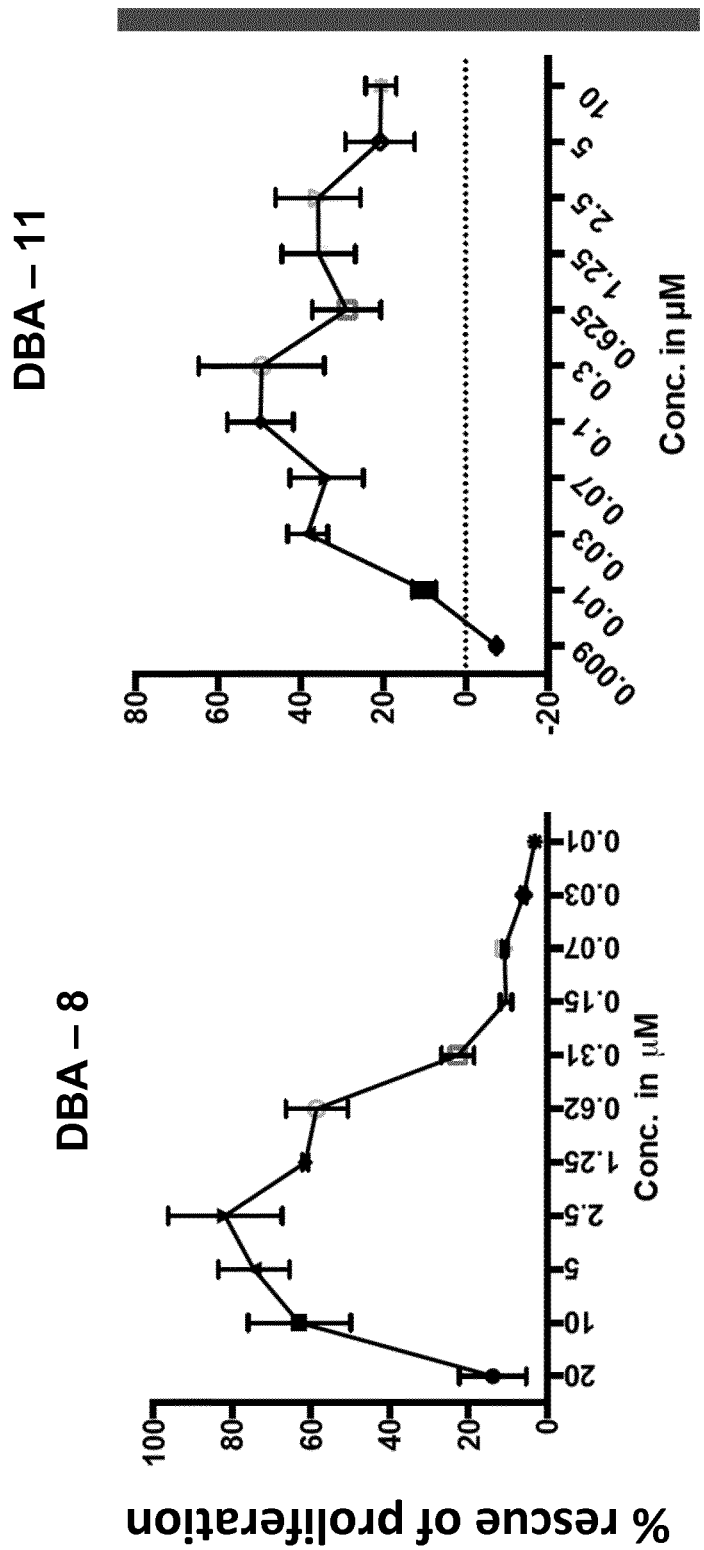

FIG. 6: The selective CDK8/CDK19 inhibitor DBA-8 shows a partial dose-dependent rescue of the proliferation defect in murine RPS19-deficient erythroid progenitor cells. This figure demonstrates that the DBA-9 analogue DBA-8 confers a partial dose-dependent rescue of proliferation in RPS19-deficient murine erythroid progenitor cells. DBA-8 has been described as Senexin A and SNX2-1-53 and is a known CDK8/CDK19 inhibitor described in Porter et al. (Nat. Acad. Sci. Proc. 2012, 109, 13799-13804) and US 2012/0071477.

Figure 7:
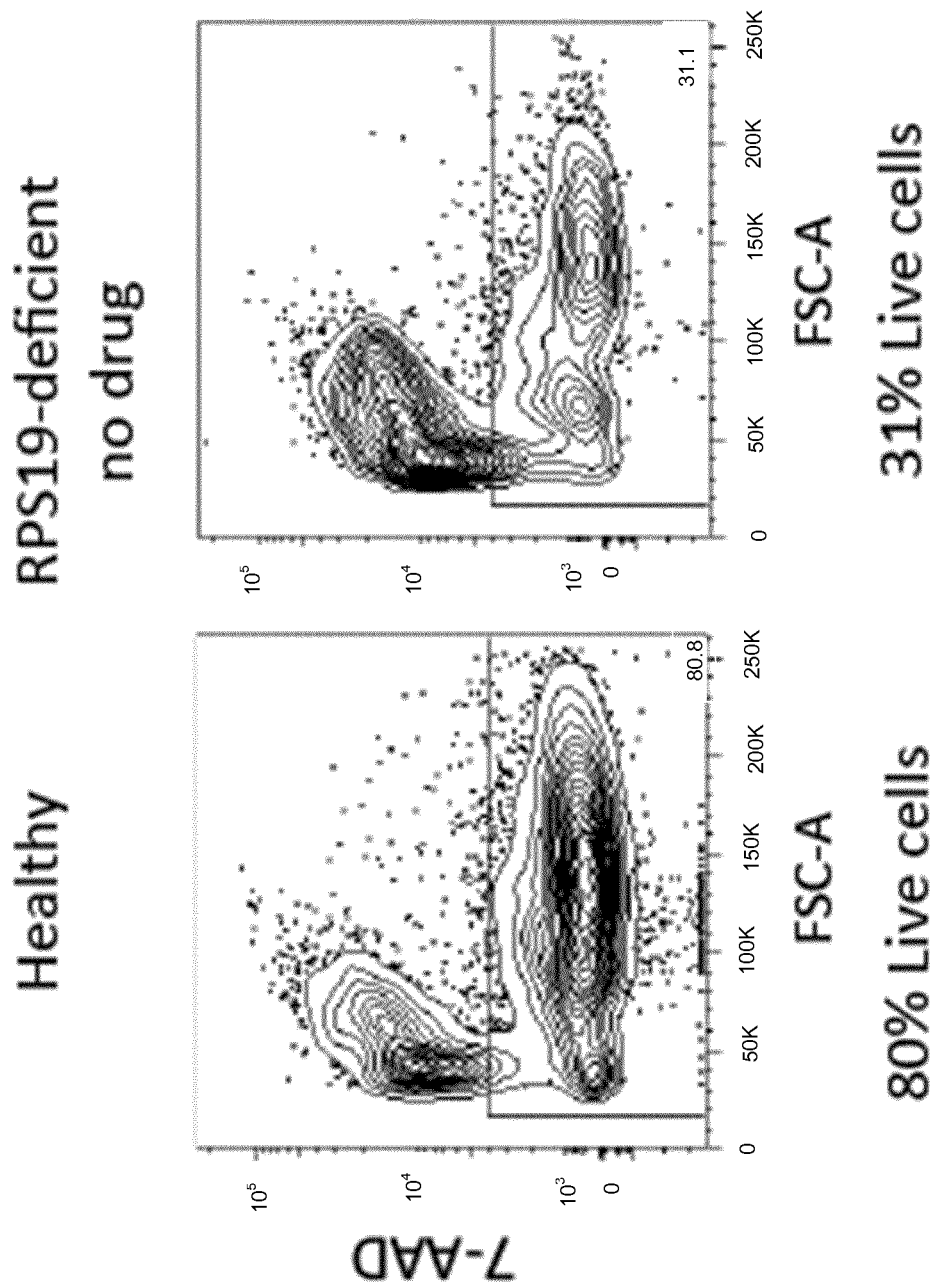
Figure 7:
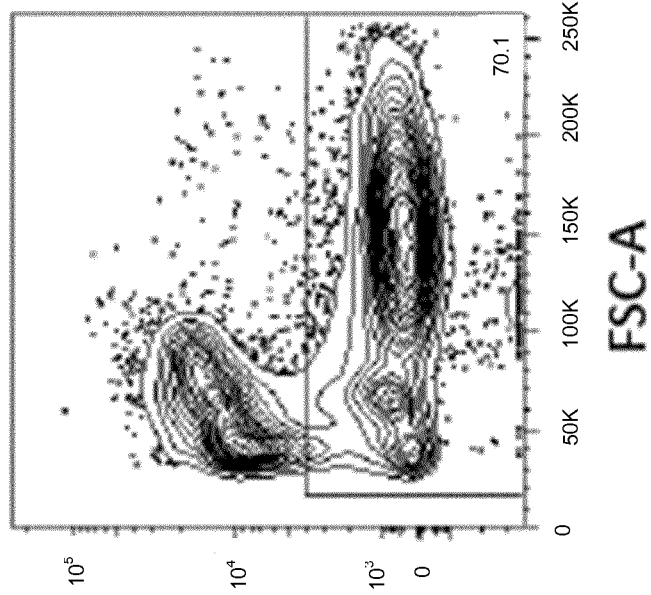
Figure 7:
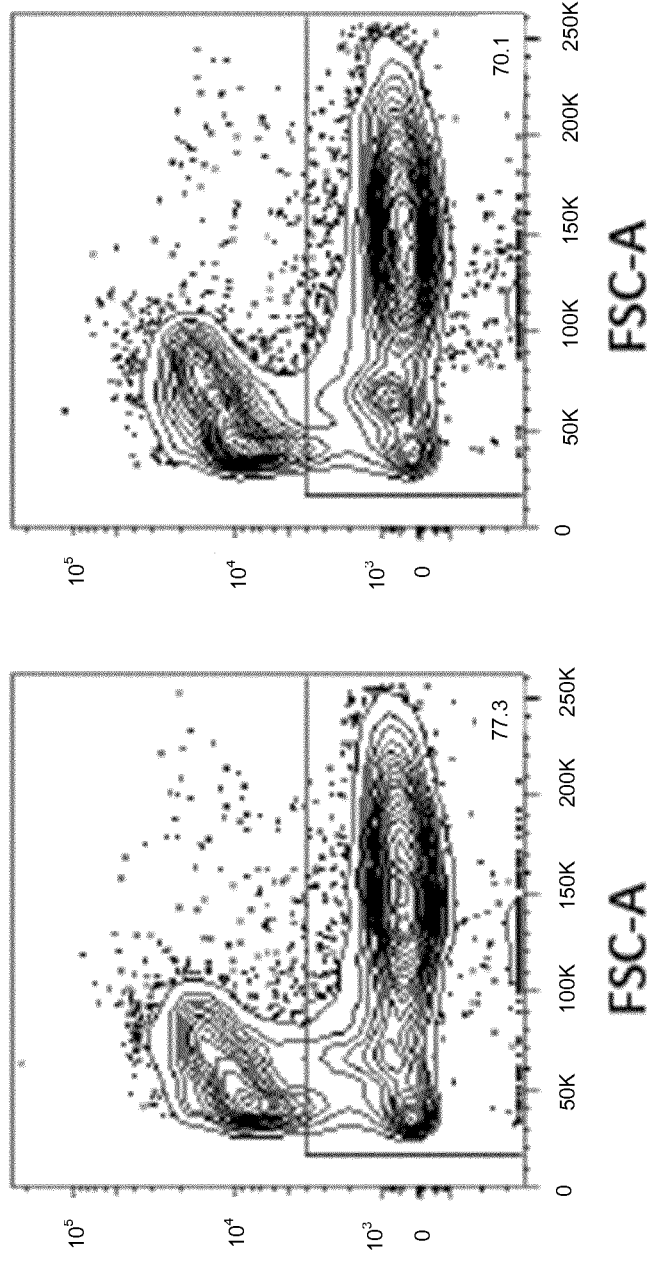

FIG. 7: The selective CDK8/CDK19 inhibitors DBA-7 and DBA-8 rescue cell survival defect in RPS19-deficient erythroid progenitors.

The Y axis of these FACS plots shows the intensity of 7-AAD, a positive marker for cell apoptosis, which is increased upon induction of RPS19-deficiency.

Figure 8:
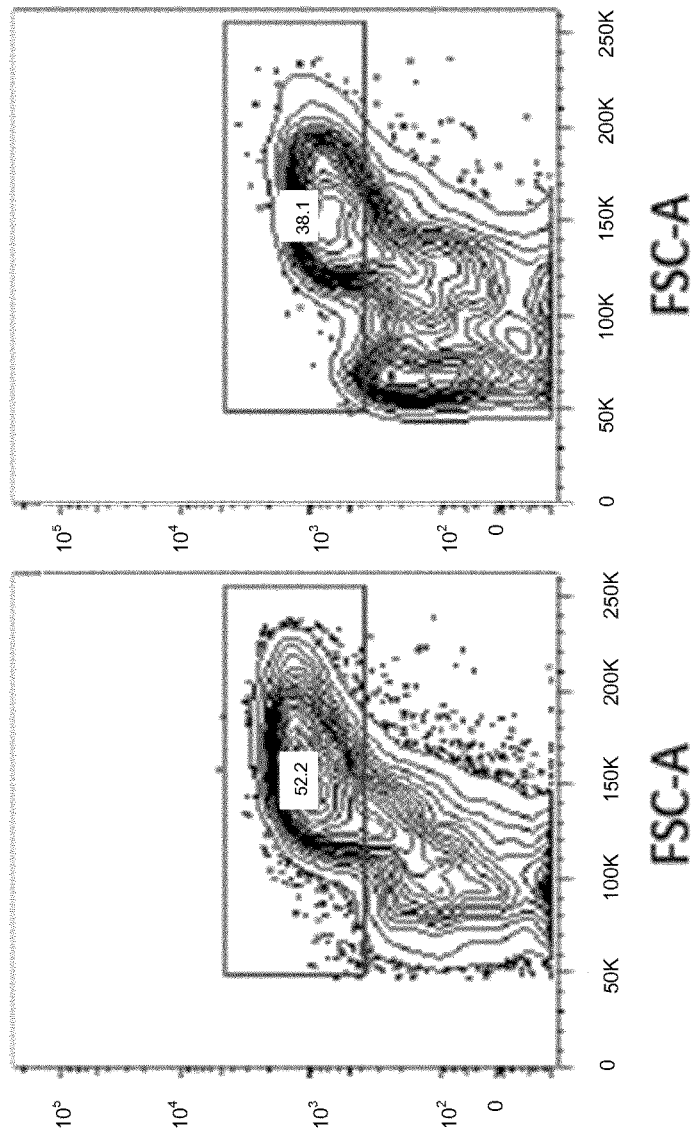
Figure 8:
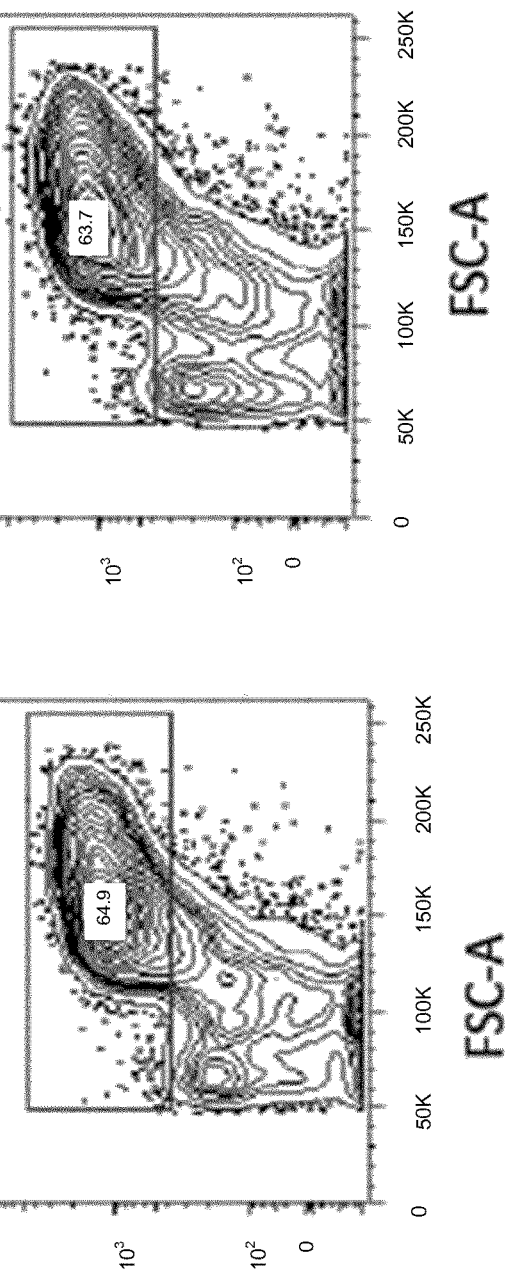

FIG. 8: The selective CDK8/CDK19 inhibitors DBA-7 and DBA-8 rescue the loss of c-kit+ progenitor cell observed in in vitro culture of RPS19-deficient erythroid progenitors. The Y axis of these FACS plots shows the intensity of c-kit, a positive marker for hematopoietic progenitor cells, a population that decreases in erythroid cultures after induction of RPS19-deficiency.

Figure 9:
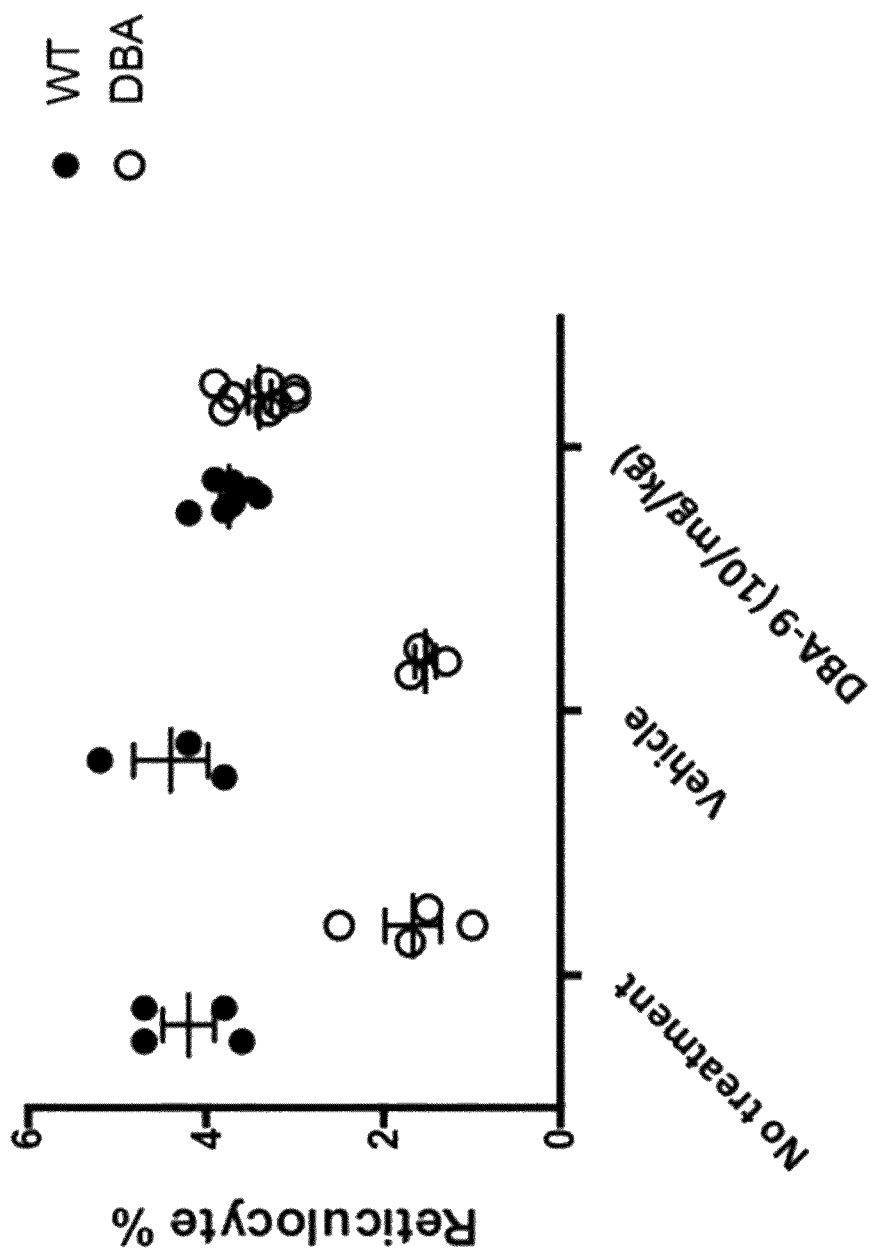

FIG. 9: The selective CDK8/CDK19 inhibitor DBA-9 improves production of erythrocytes in vivo in a RPS19-deficient mouse model for DBA.

Figure 10:
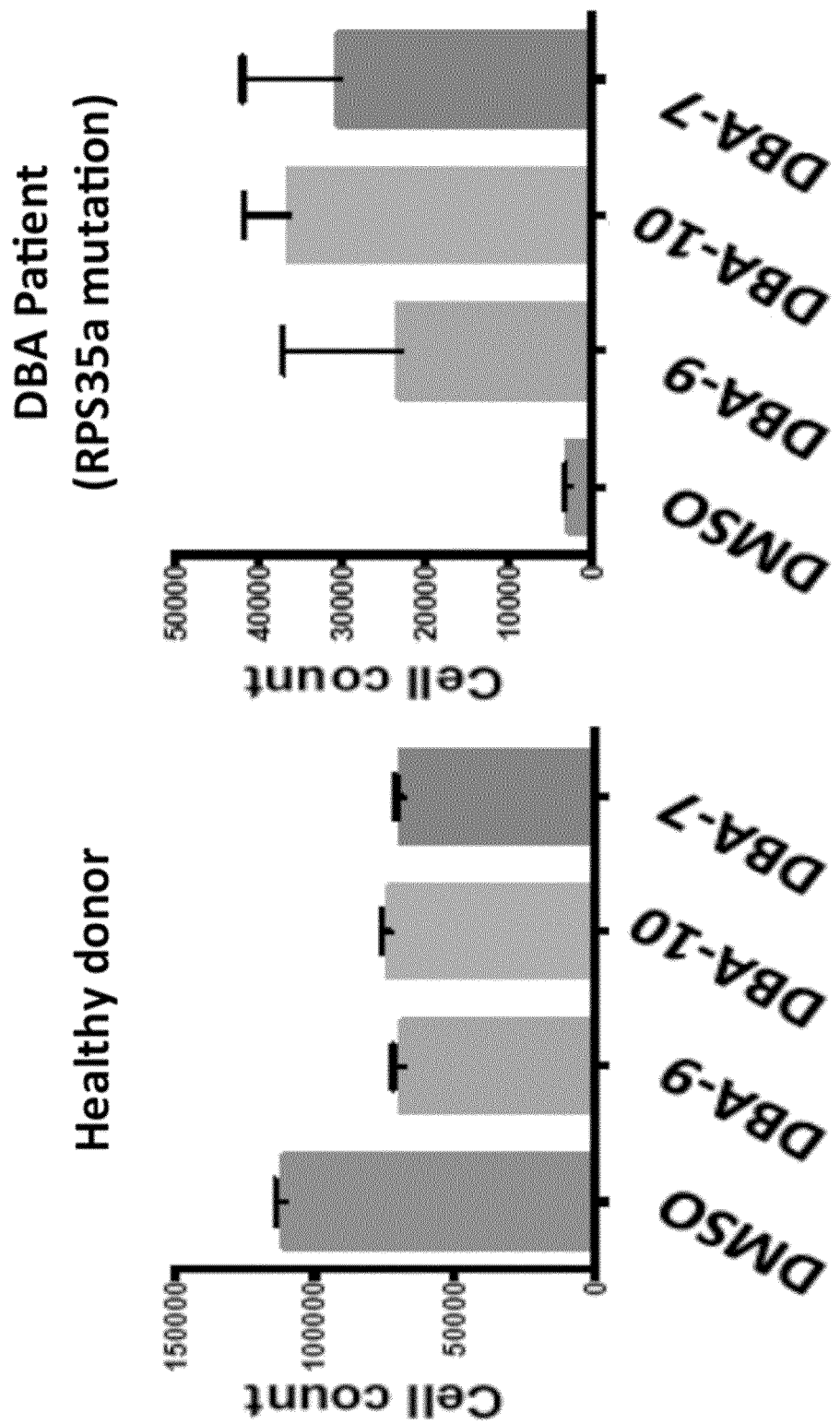
Figure 11:
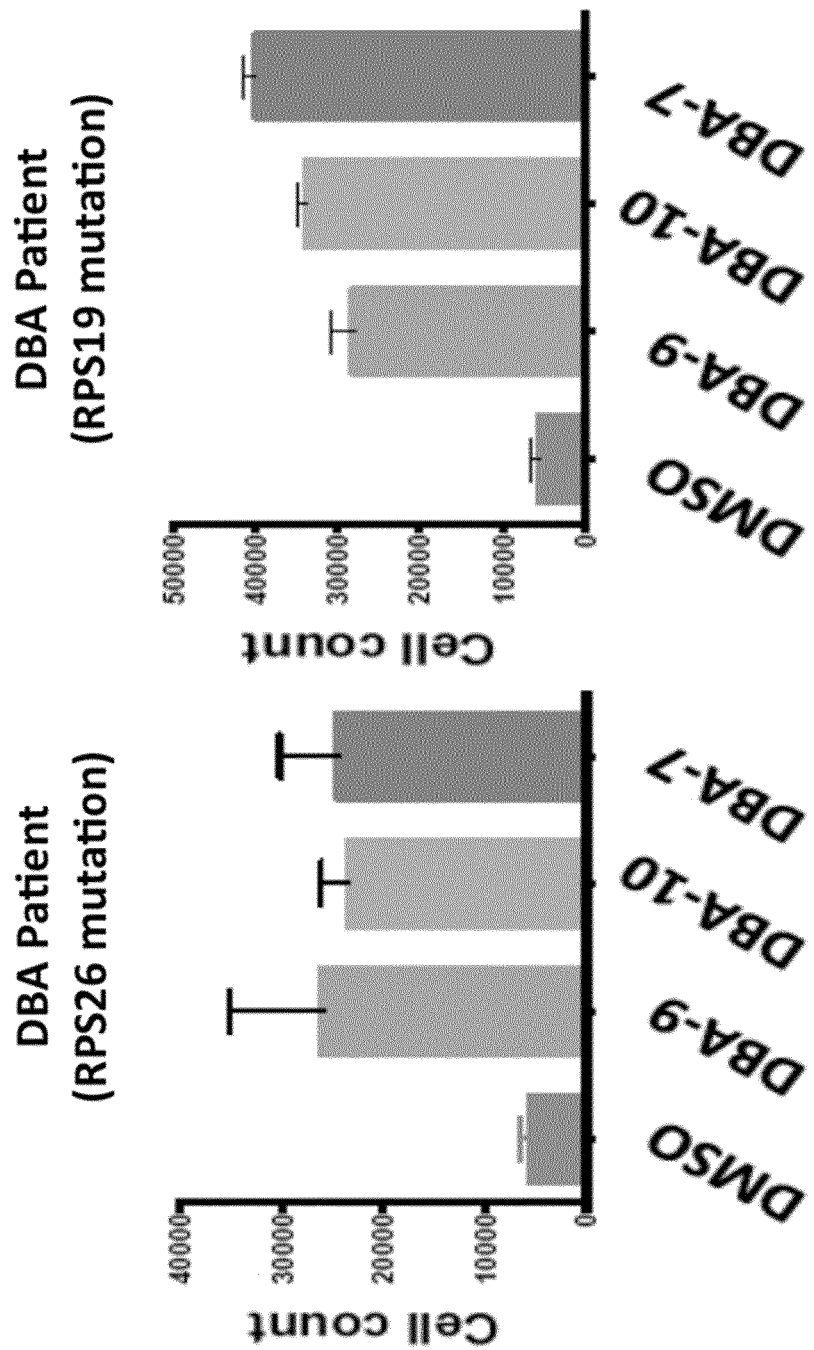

FIG. 10 and FIG. 11: The selective CDK8/CDK19 inhibitors DBA-7, DBA-9 and DBA-10 rescue proliferation of erythroid DBA patient cells in vitro.

5000 peripheral blood CD34+ cells from healthy donors or DBA patients were plated in serum free medium containing human stem cell factor and Epo to support expansion of erythroid progenitors and precursor cells. DMSO or 200 nM of DBA-7, DBA-9 or DBA-10 were added to the culture medium. The Y-axis shows cell counts at day 14 of culture. All three CDK8-inhibitors promote proliferation of DBA patient cells.

Figure 12:
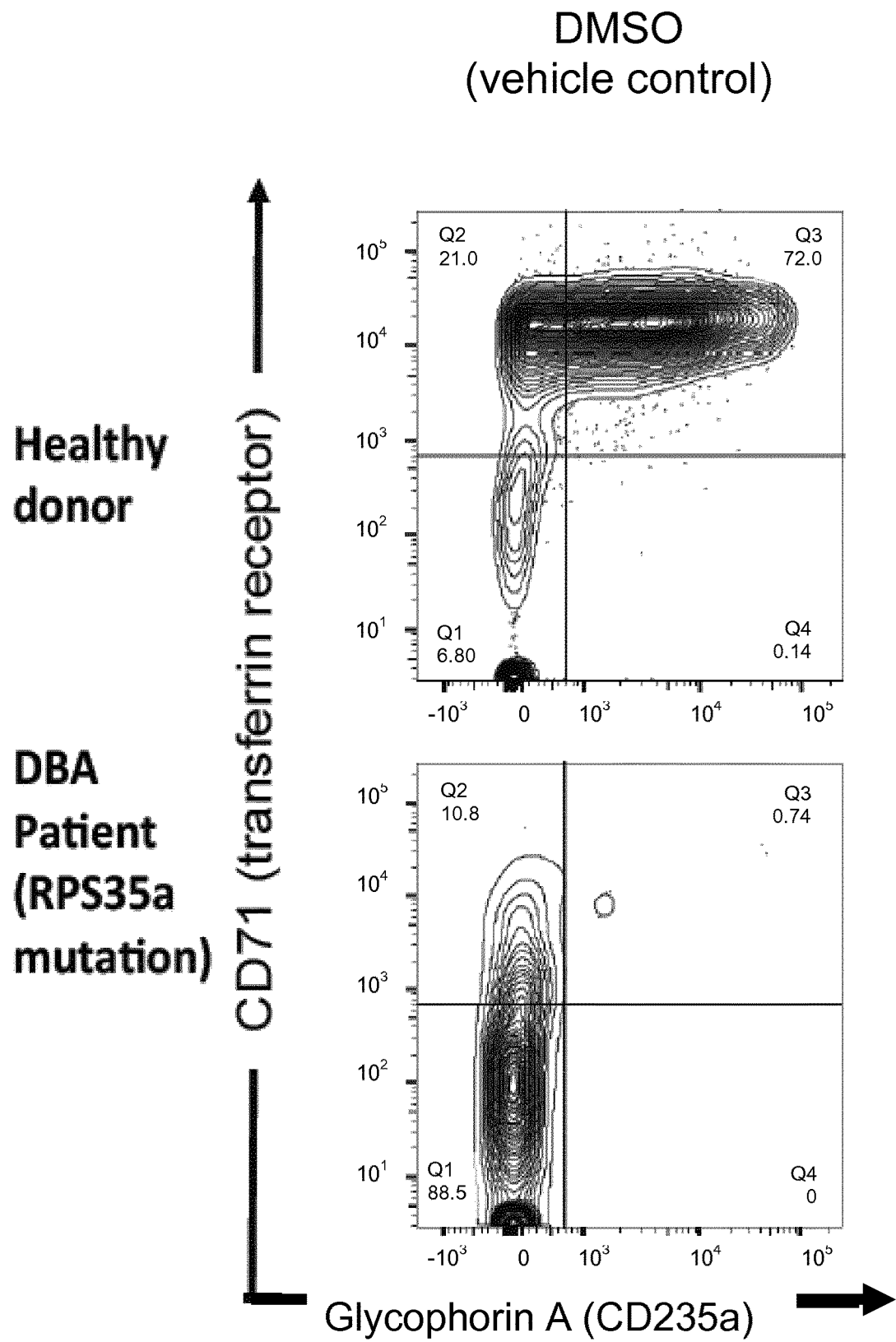
Figure 12:
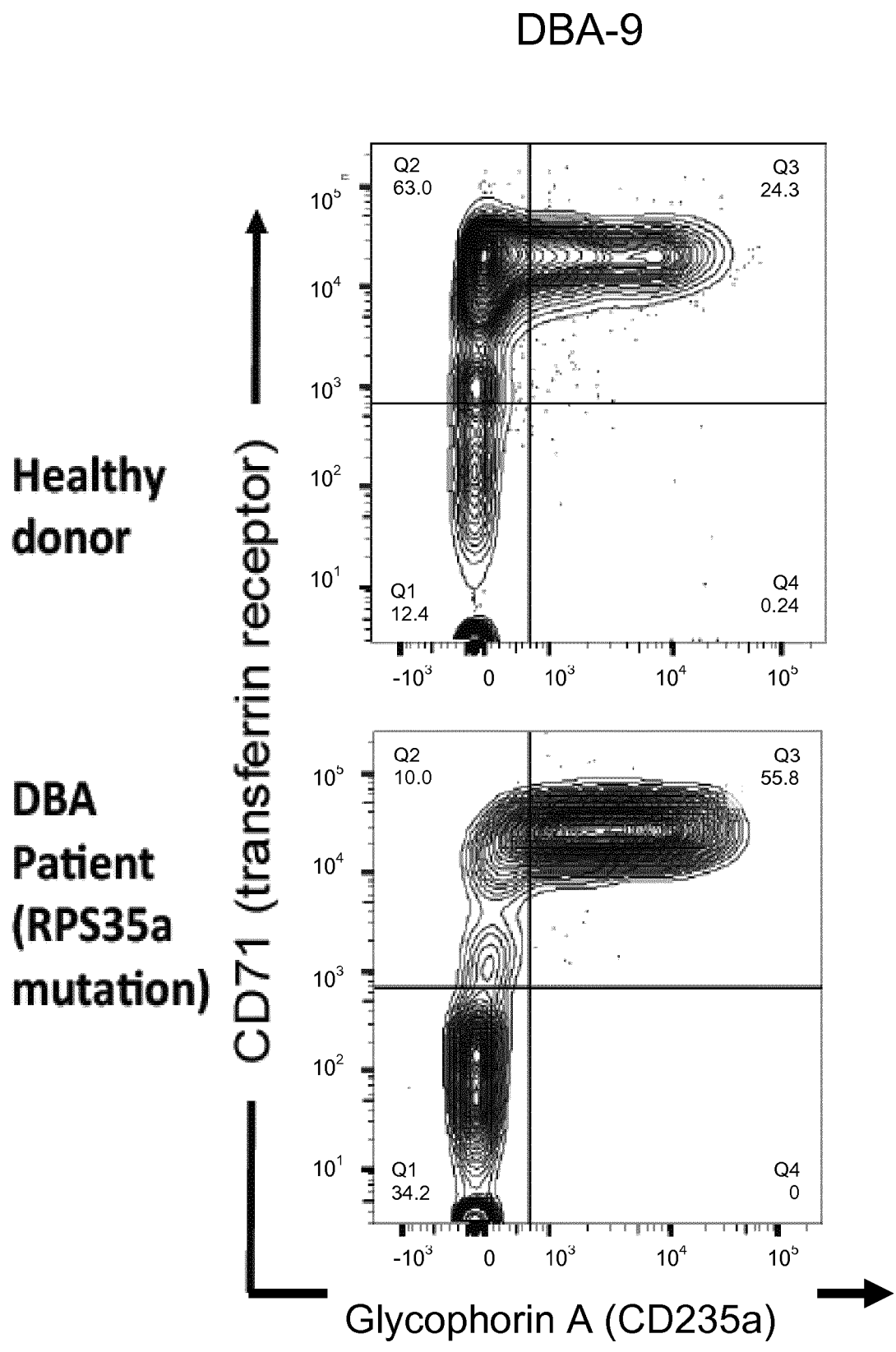
Figure 12:
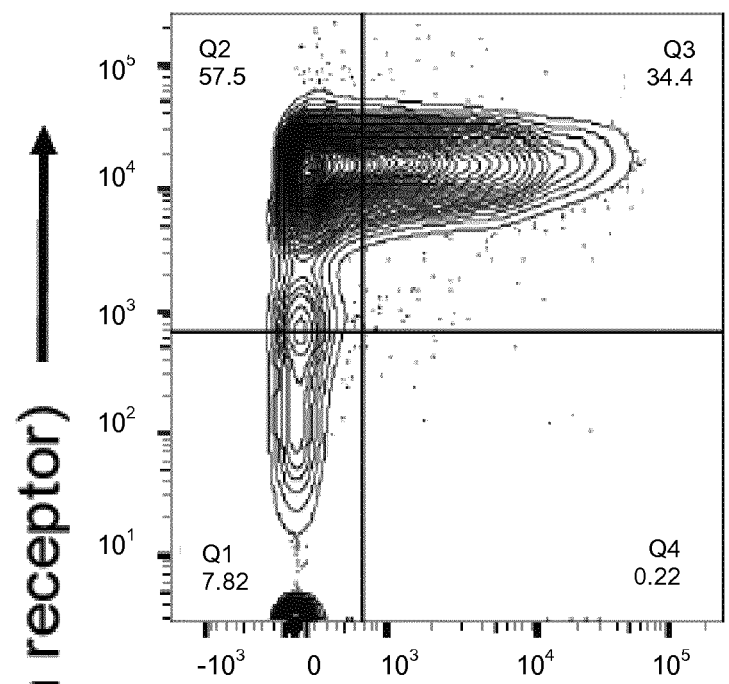
Figure 12:
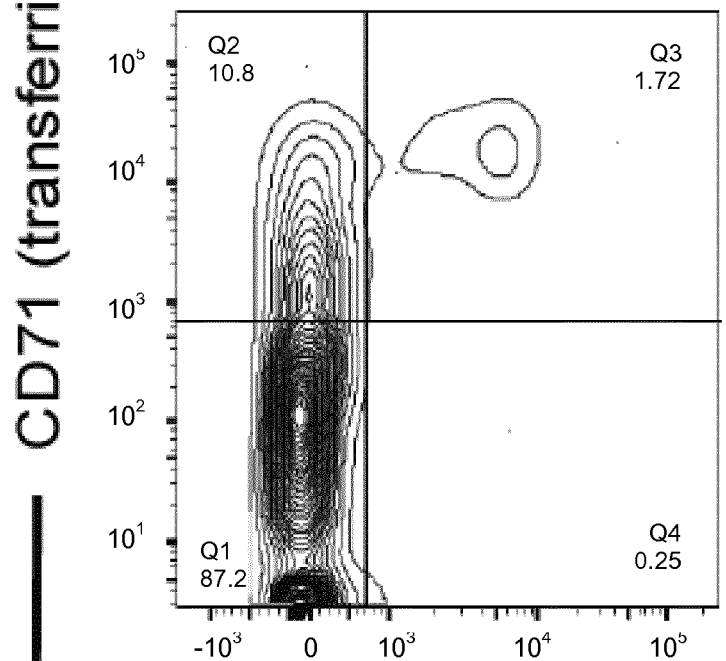
Figure 12:
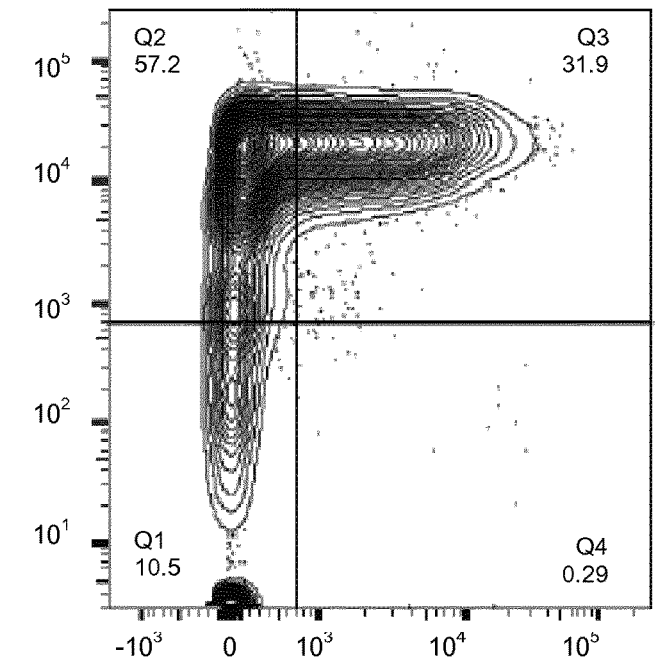
Figure 12:
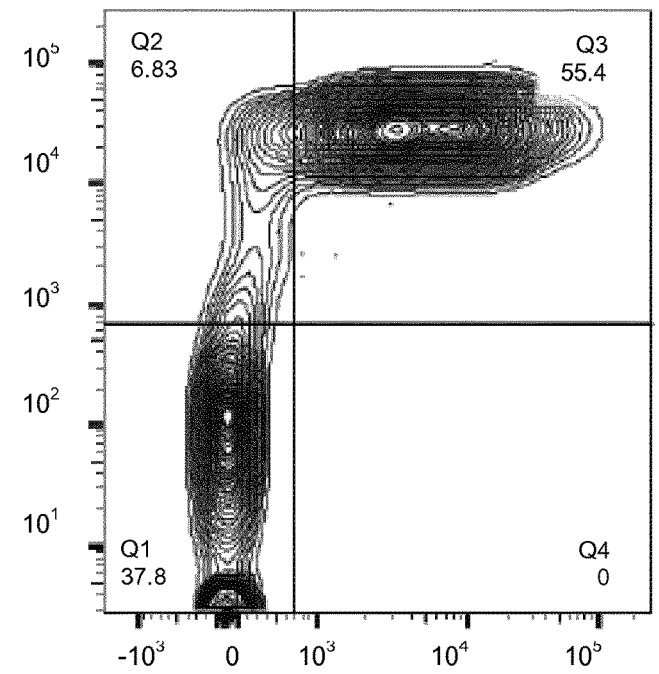
Figure 13:
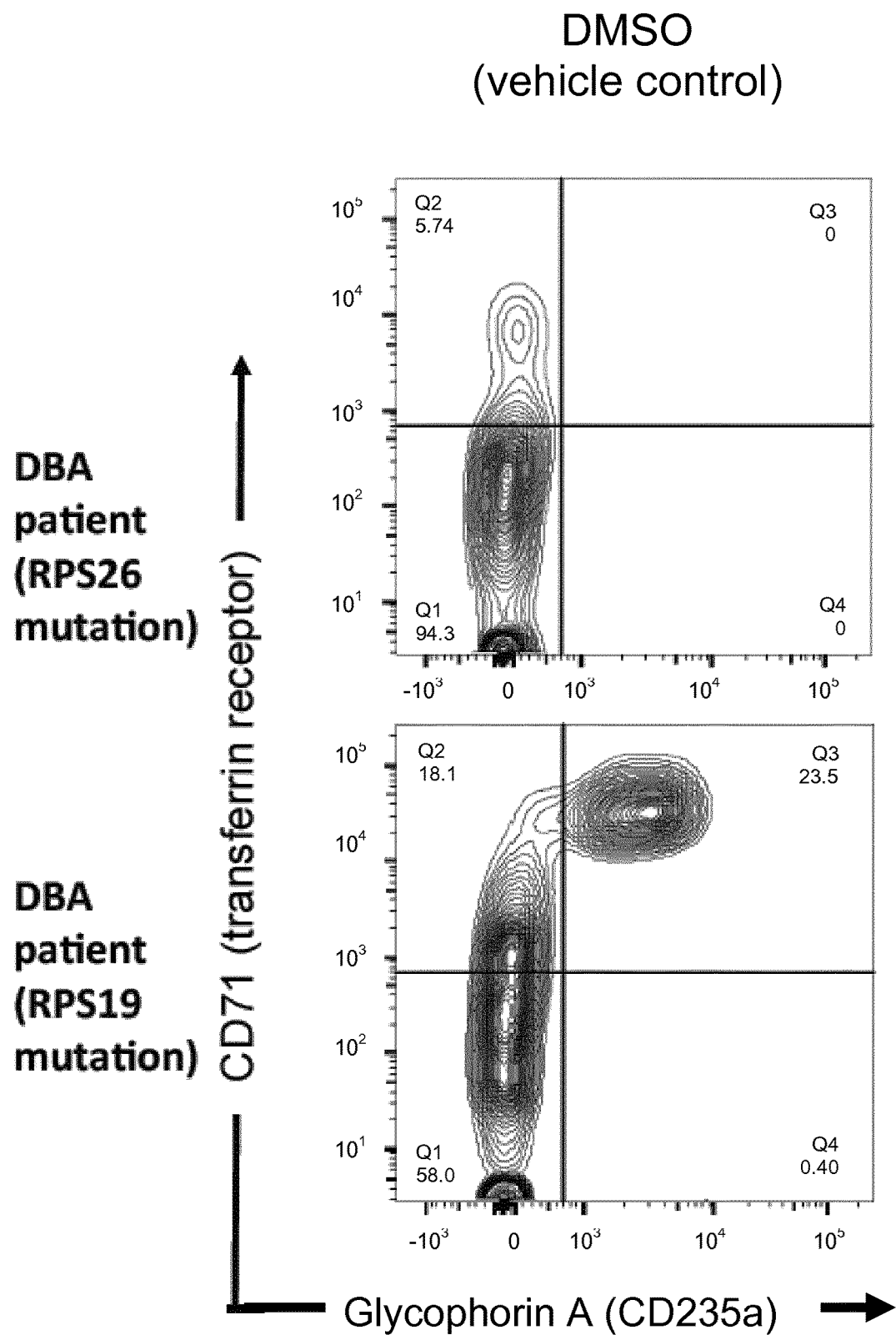
Figure 13:
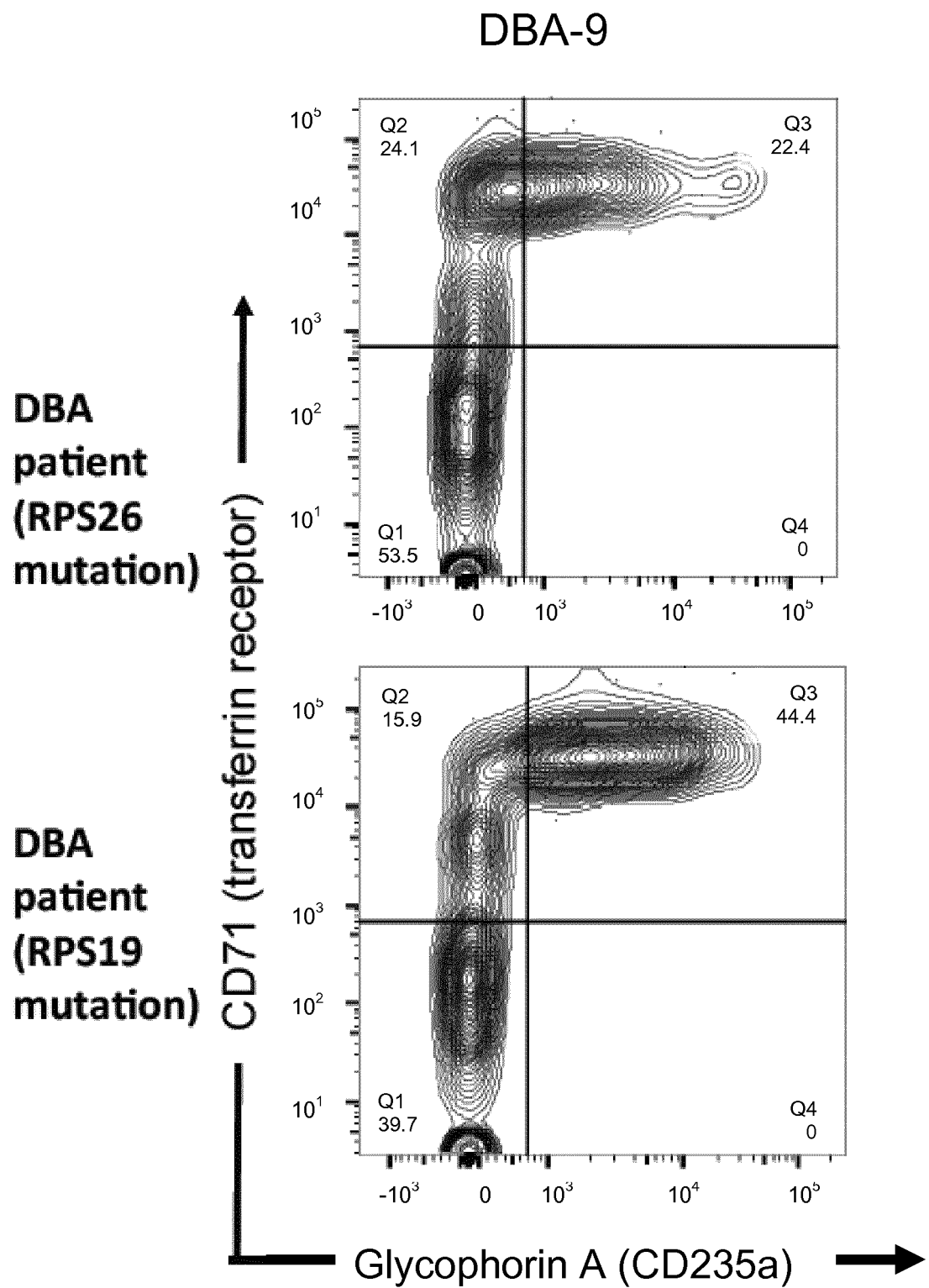
Figure 13:
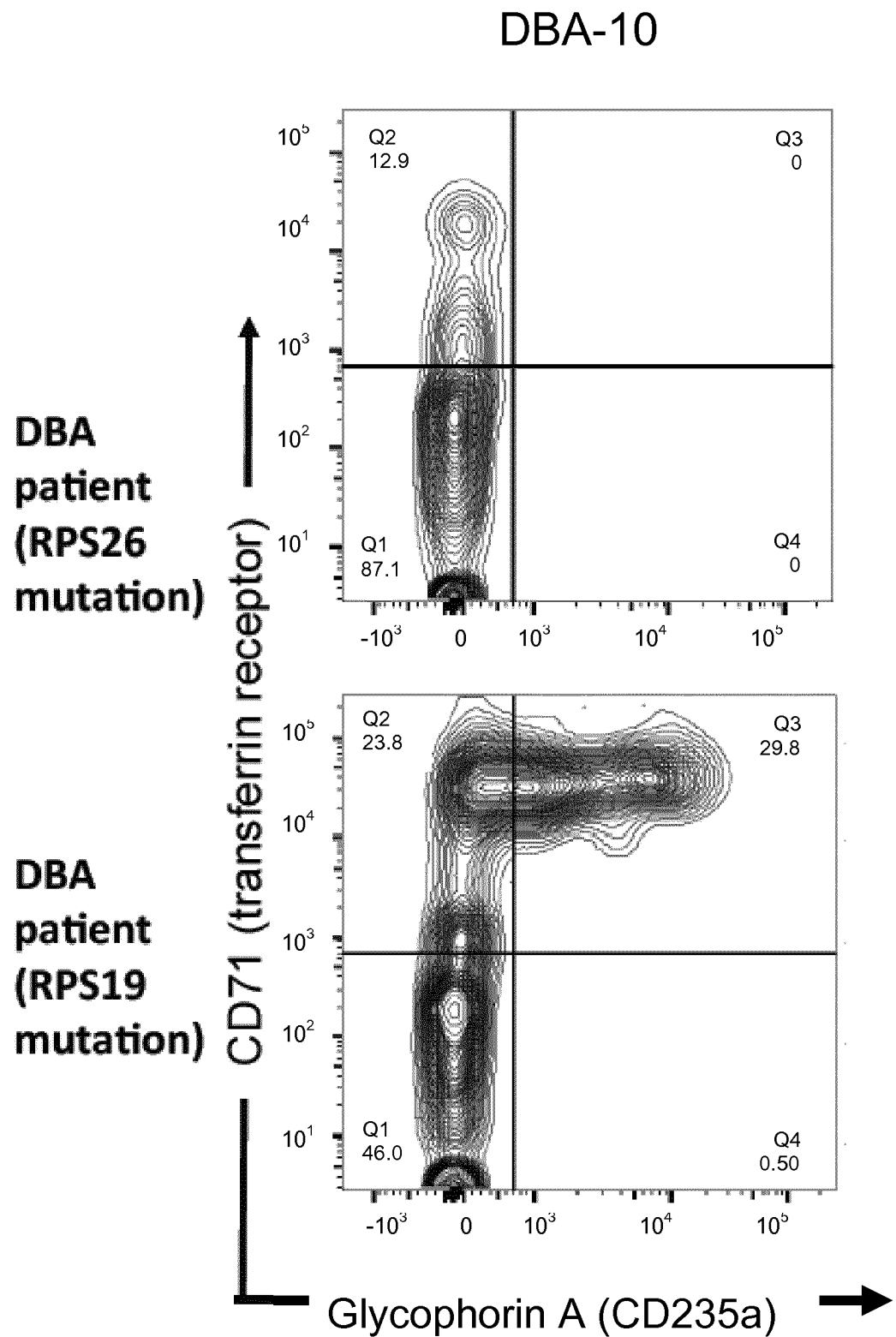
Figure 13:
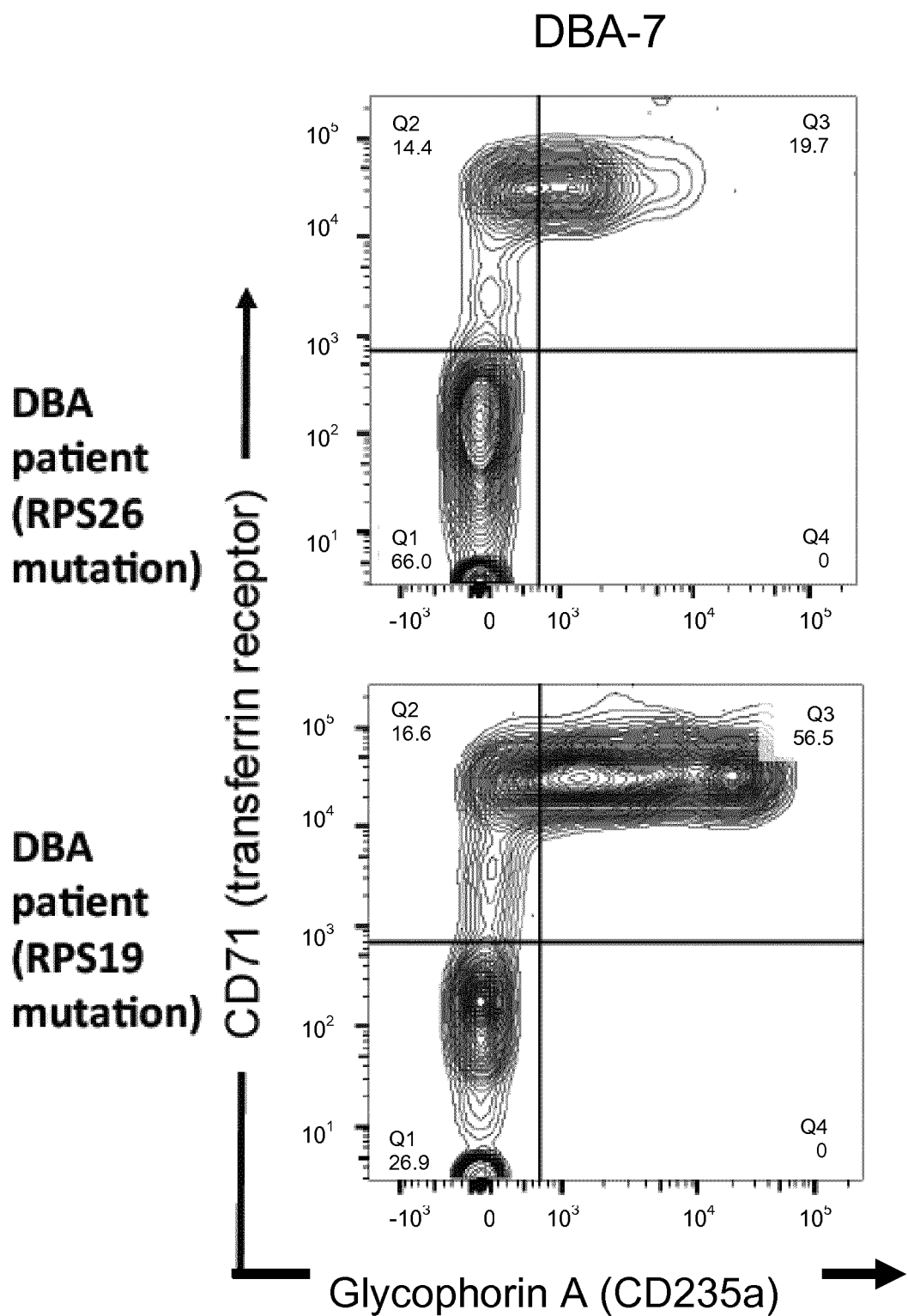

FIG. 12 and FIG. 13: The selective CDK8/CDK19 inhibitors DBA-7, DBA-9 and DBA-10 rescue erythroid maturation of DBA patient cells in vitro.

Cells were cultured in the same conditions as in FIG. 9 and analysed by flow cytometry at day 8 of culture. CD71 is a positive marker for early erythroid progenitors while CD71 and CD235a positive cells are mature erythroid precursors. DBA-7, DBA-9 and DBA-10 increase erythroid maturation of DBA patient cells compared to DMSO.

DETAILED DESCRIPTION OF THE INVENTION

Definitions

The term "CDK8" as used herein refers to cyclin dependent kinase 8. The sequence of human CDK8 is available under the accession number NP_001251.1.

The term "CDK19" as used herein refers to cyclin dependent kinase 19. The sequence of human CDK19 is available under the accession number NP_055891.1.

The term "CDK8 and/or CDK19 inhibitor" as used herein refers to a compound which is capable of inhibiting CDK8 and CDK19. In particular, a CDK8 and/or CDK19 inhibitor may be a compound capable of inhibiting the kinase activity of at least one of CDK8 and CDK19.

The term "ribosomopathies" as used herein refers to diseases caused by alterations in the structure or function of ribosomal component proteins and/or rRNA, or in the structure or functions of other genes whose products are involved in ribosome biogenesis. Thus, ribosomopathy may be a disease caused at least in part by failure in ribosome biogenesis.

Method for Treatment of a Clinical Condition

The present invention provides CDK8 and/or CDK19 inhibitors for use in the treatment of clinical condition selected from the group consisting of ribosomopathies and diseases and disorders caused by increased apoptosis of hematopoietic stem cells and/or progenitor cells.

The CDK8 and/or CDK19 inhibitor of the invention may be any compound capable of inhibiting the activity of CDK8 and/or CDK19, such as any of the compounds described herein below in the section CDK8 and/or CDK19 inhibitor. In particular the CDK8 and/or CDK19 may be any of the compounds of formulas (I), (XIV), (XV), (XVII) or (XVIII) described herein below.

The clinical condition may be any of the clinical conditions described herein below in the section "Clinical condition".

Clinical Condition

The present invention provides CDK8 and/or CDK19 inhibitors for treatment of clinical conditions associated with CDK8 and/or CDK19.

In one embodiment of the invention said clinical condition is a ribosomopathy or a disease caused by increased apoptosis of hematopoietic stem cells and/or progenitor cells.

In one embodiment of the invention the ribosomopathy is anemia, e.g. aplastic anemia. In particular, the ribosomopathy may be a constitutional aplastic anemia. Thus, the ribosomopathy may be a disease classified under D61.0 of WHO's ICD-10 classification.

In one embodiment of the invention the clinical condition to be treated with a CDK8 and/or CDK19 inhibitor according to the invention is Diamond-Blackfan anemia (DBA). DBA is an example of a ribosomopathy classified under D61.0.

In one embodiment the invention relates to CDK8 and/or CDK19 inhibitors for use in the treatment of Diamond-Blackfan anemia (DBA), wherein said CDK8 and/or CDK19 inhibitors at least partly rescue cellular hypoproliferation causing anemia in DBA. Preferably, said CDK8 and/or CDK19 inhibitors rescue cellular hypoproliferation causing anemia in DBA. It may for example be determined whether a CDK8 and/or CDK19 inhibitor rescues hypoproliferation by determining whether said CDK8 and/or CDK19 inhibitor upon administration to an individual suffering from DBA restore haemoglobin levels to a normal level, for example to a level of at least 100 g/L. Another example of a ribosomopathy, which can be treated with a CDK8 and/or CDK19 inhibitor according to the invention is Shwachman-Diamond syndrome.

In another embodiment the clinical condition to be treated with a CDK8 and/or CDK19 inhibitor according to the invention is a clinical condition classified under D64.4 using WHO's ICD-10 classification. Non-limiting examples of such conditions includes congenital dyserythopoietic anaemia, such as Dyshaematopoietic anaemia (congenital).

In another embodiment the clinical condition to be treated with a CDK8 and/or CDK19 inhibitor according to the invention is a clinical condition classified under Q75.4 using WHO's ICD-10 classification. Non-limiting examples of such conditions includes Mandibulofacial dysostosis, for example Treacher-Collins syndrome.

In another embodiment the clinical condition to be treated with a CDK8 and/or CDK19 inhibitor according to the invention is a clinical condition classified under Q78.8 using WHO's ICD-10 classification. Non-limiting examples of such conditions includes Cartilage-hair hypoplasia.

In another embodiment the clinical condition to be treated with a CDK8 and/or CDK19 inhibitor according to the invention is a clinical condition classified under Q82.8 using WHO's ICD-10 classification. Non-limiting examples of such conditions includes congenital malformations of skin, for example Dyskeratosis congenital.

In another embodiment the clinical condition to be treated with a CDK8 and/or CDK19 inhibitor according to the invention is a clinical condition classified under Q96 using WHO's ICD-10 classification. Non-limiting examples of such conditions includes Turner's syndrome.

In another embodiment of the invention the ribosomopathy is selected from the group consisting of 5q-myelodysplastic syndrome, North American Indian childhood cirrhosis, Isolated congenital asplenia, and Bowen-Conradi syndrome.

The clinical condition to be treated with a CDK8 and/or CDK19 inhibitor according to the invention may also be a disease characterized by reduced number of hematopoietic stem cells and/or progenitor cells. Such clinical conditions may for example be a disease caused by induced apoptosis in hematopoietic stem cells and/or progenitor cells. Such clinical conditions may for example also be a disease caused by hypoproliferation of hematopoietic stem cells and/or progenitor cells.

Thus, the clinical condition may also be an immunodeficiency growth retardation, a bone marrow failure diseases or immuno-deficiencies such as Schwachman-Diamond Syndrome, Dyskeratosis congenita, Cartilage-hair hypoplasia, Treacher-Collins syndrome or Turner's syndrome.

In one embodiment of the invention the ribosomopathy is selected from the group consisting of Diamond-Blackfan anemia, Dyskeratosis congenita, Shwachman-Diamond syndrome, 5q-myelodysplastic syndrome, Treacher Collins syndrome, Cartilage-hair hypoplasia, North American Indian childhood cirrhosis, Isolated congenital asplenia, Bowen-Conradi syndrome, Turners syndrome and Fanconi's anemia.

In certain embodiments of the invention, the invention provides particular CDK8 and/or CDK19 inhibitors for therapies aimed at promoting osteogenesis. In such embodiments of the invention, the CDK8 and/or CDK19 inhibitor may in particular be any of the compounds of formulas (I), (XIV), (XV), (XVII) or (XVIII) described herein below.

The bone anabolic disorder may for example be selected from the group consisting of osteopathy and osteoarthritis.

Said osteopathy may for example be selected from the group consisting of osteoporosis, osteopenia or bone destruction associated with rheumatoid arthritis, Paget's disease of bone, bone fracture or dysostosis due to dwarfism.

For example, CDK8 and/or CDK19 inhibitors may be used for treatment of any clinical condition classified under M80-M85 using WHO's ICD-10 classification. Thus, the CDK8 and/or CDK19 inhibitors may be used in the treatment of disorders of bone density and structure. Said disorders of bone density and structure may for example be selected from the group consisting of Osteoporosis with pathological fracture, osteoporotic vertebral collapse and wedging, postmenopausal osteoporosis with pathological fracture, postoophorectomy osteoporosis with pathological fracture, osteoporosis of disuse with pathological fracture, postsurgical malabsorption osteoporosis with pathological fracture, drug-induced osteoporosis with pathological fracture, idiopathic osteoporosis with pathological fracture, unspecified osteoporosis with pathological fracture, osteoporosis without pathological fracture, postmenopausal osteoporosis, postoophorectomy osteoporosis, osteoporosis of disuse, postsurgical malabsorption osteoporosis, drug-induced osteoporosis, idiopathic osteoporosis, localized osteoporosis, senile osteoporosis, uspecified osteoporosis, osteoporosis in diseases classified elsewhere, osteoporosis in multiple myelomatosis, osteoporosis in endocrine disorders, adult osteomalacia, puerperal osteomalacia, senile osteomalacia, adult osteomalacia due to malabsorption, postsurgical malabsorption osteomalacia in adults, adult osteomalacia due to malnutrition, aluminium bone disease, other drug-induced osteomalacia in adults, unspecified adult osteomalacia, disorders of continuity of bone, malunion of fracture, nonunion of fracture, delayed union of fracture, stress fracture, pathological fracture, fibrous dysplasia, skeletal fluorosis, hyperostosis of skull, osteitis condensans, solitary bone cyst, aneurysmal bone cyst, other cyst of bone, hyperostosis of bones and osteosclerosis.

In one embodiment the CDK8 and/or CDK19 inhibitors may be for treatment of osteoporosis. Said osteoporosis may for example be postmenopausal osteoporosis, senile osteoporosis or secondary osteoporosis caused by the use of steroids or immunosuppressants.

CDK8 and/or CDK19 inhibitors can be used in the treatment of other bone-related clinical conditions including treatment of osteolysis, healing of bone fractures, postsurgical bone healing and prevention of prosthetic loosening.

CDK8 and/or CDK19 Inhibitor

The invention relates to CDK8 and/or CDK19 inhibitors for use in treatment of the clinical conditions outlined in the section "Clinical condition".

The CDK8 and/or CDK19 inhibitor may be any compound capable of inhibiting CDK8 and/or CDK19. In particular, the CDK8 and/or CDK19 inhibitor may be any compound capable of inhibiting the kinase activity of CDK8 and/or CDK19.

Whether a compound is capable of inhibiting CDK8 and/or CDK19 may be determined using any suitable assay, for example an assay for kinase activity. An assay for kinase activity of CDK8 and/or CDK19 may for example comprise the steps of:

a) Incubating the following under conditions allowing for activity of CDK8 and/or CDK19
   a. a substrate for CDK8 and/or CDK19, which for example may be the carboxy-terminal domain (CTD) of the largest subunit of RNA polymerase II;
   b. CDK8 and/or CDK19 typically together with cyclin C
   c. ATP, for example ATP comprising radioactively labelled phosphate
   d. a putative inhibitor b) determining whether said substrate is phosphorylated, e.g. by determining whether radioactively labelled phosphate is transferred to the substrate wherein if phosphorylation of the substrate is inhibited, then said putative inhibitor is a CDK8 and/or CDK19 inhibitor.

An assay for kinase activity of CDK8 may for example comprise the steps of:

a) Incubating the following under conditions allowing for activity of CDK8
   a. a substrate for CDK8, which for example may be, which in the case of CDK8 for example may be the carboxy-terminal domain (CTD) of the largest subunit of RNA polymerase II;
   b. CDK8 typically together with cyclin C
   c. ATP, for example ATP comprising radioactively labelled phosphate
   d. a putative CDK8 inhibitor b) determining whether said substrate is phosphorylated, e.g. by determining whether radioactively labelled phosphate is transferred to the substrate wherein if phosphorylation of the substrate is inhibited, then said putative CDK8 inhibitor is a CDK8 inhibitor.

In one embodiment a compound is considered to be a CDK8 and/or CDK19 inhibitor if said compound can selectively bind to CDK8 and/or CDK19. In particular, a compound is considered to be a CDK8 and/or CDK19 inhibitor if said compound can bind to CDK8 and/or CDK19 with a $K_D$ of at the most of 500 µM, such as at the most of 400 µM, such as at the most of 300 µM, such as at the most of 200 µM, such as at the most of 100 µM, such as at the most of 50 µM, such as at the most of 10 µM, such as at the most of 1 µM, such as at the most of 500 nM, such as at the most of 400 nM, for example at the most of 300 nM, for example at the most 200 nM, such as at the most 100 nM. By "selective" is generally meant that the CDK8 and/or CDK9 inhibitor does not exhibit harmful off-target effects which may affect the clinical efficacy of the inhibitor, nor is the CDK8 and/or CDK9 inhibitor toxic in clinically effective concentrations.

One useful way of determining whether a compound is a CDK8 and/or CDK19 inhibitor is to use the KinomeScan assay, which is commercially available from DiscoverX, United States. In particular, a compound may be considered to be a CDK8 and/or CDK19 inhibitor if it can inhibit CDK8 and/or CDK19 at a concentration as defined herein above using the KinomeScan assay.

The CDK8 and/or CDK19 inhibitor according to the invention may for example be:
  i) any of the compounds of formula (I) described herein below in the section "CDK8 and/or CDK19 inhibitors of formula (I),
  ii) any of the compounds of formula (XIV) or (XV) described herein below in the section "CDK8 and/or CDK19 inhibitors of formula (XIV) or (XV),
  iii) any of the compounds of formula (XVII) described herein below in the section "CDK8 and/or CDK19 inhibitors of formula (XVII)

In one embodiment of the invention the CDK8 and/or CDK19 inhibitors may be any of the CDK8 inhibitors described in WO2014/029726 which is hereby incorporated by reference. In particular the CDK8 and/or CDK19 inhibitor may any of the compounds of formula I of WO 2014/029726 described therein, for example any of the compounds mentioned in Table 1 of WO 2014/029726.

In one embodiment of the invention the CDK8 and/or CDK19 inhibitors may be any of the CDK8 inhibitors described in WO 2014/090692 which is hereby incorporated by reference. In particular the CDK8 and/or CDK19 inhibitor may any of the compounds of formula I of WO 2014/090692 described therein, for example any of the compounds mentioned in Table 1 of WO 2014/090692.

In one embodiment of the invention the CDK8 and/or CDK19 inhibitors may be any of the CDK8 inhibitors described in WO2014/106606 which is hereby incorporated by reference. In particular the CDK8 and/or CDK19 inhibitor may any of the compounds of formula I of WO 2014/106606 described therein, for example any of the compounds mentioned in Table 1 of WO 2014/106606.

In one embodiment of the invention the CDK8 and/or CDK19 inhibitors may be any of the CDK8 inhibitors described in WO 2014/154723 which is hereby incorporated by reference. In particular the CDK8 and/or CDK19 inhibitor may any of the compounds of formula I of WO 2014/154723 described therein, for example any of the compounds mentioned in Table 1 of WO 2014/154723.

In one aspect, the present invention concerns a compound selected from the compounds of any one of the general formulas (XVII), (XIV), (XV), (XVIII) and (I), for use in the treatment of a ribosomopathy, and/or a disease characterized by reduced number of hematopoietic stem cells and/or progenitor cells as described herein.

In one aspect, the present invention concerns a compound selected from the compounds of any one of the general formulas (XVII), (XIV), (XV), and (XVIII), for use in the treatment of a bone anabolic disorder as described herein.

In one embodiment the compound of the invention is selected from the group consisting of the compounds mentioned in Table 1 below.

TABLE 1

| Compound name | Structure | $EC_{50}$ (μM) | $EC_{MAX}$ (% rescue) |
|---|---|---|---|
| DBA-1 | 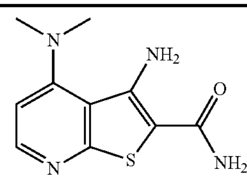 | 1.2 | 25 |
| DBA-2 | 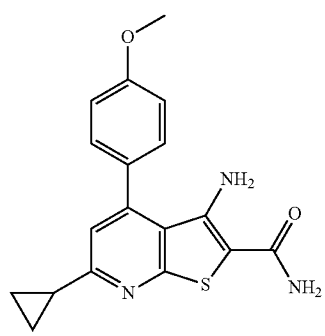 [SMILES: COc1ccc(-c2cc(C3CC3)nc3sc(C(N)=O)c(N)c23)cc1] | 15 | 45 |
| DBA-3 | 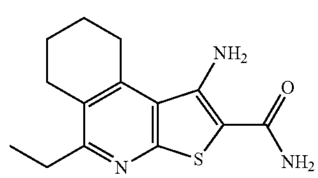 [SMILES: CCc1nc2sc(C(N)=O)c(N)c2c2c1CCCC2] | 11 | 38 |
| DBA-4 | 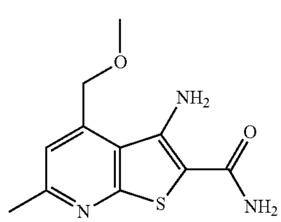 [SMILES: COCc1cc(C)nc2sc(C(N)=O)c(N)c12] | 2.8 | 28 |

TABLE 1-continued

| Compound name | Structure | EC$_{50}$ (μM) | EC$_{MAX}$ (% rescue) |
|---|---|---|---|
| DBA-5 | 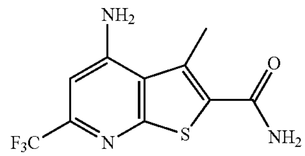 | 1.7 | 21 |
| DBA-6 | 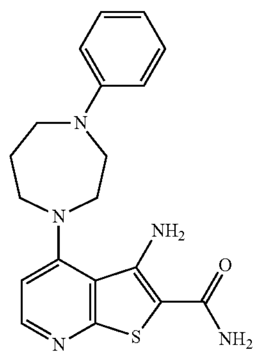 [SMILES: NC(=O)c1sc2nccc(N3CCCN(c4ccccc4)CC3)c2c1N] | 0.18 | 30 |
| DBA-7 | 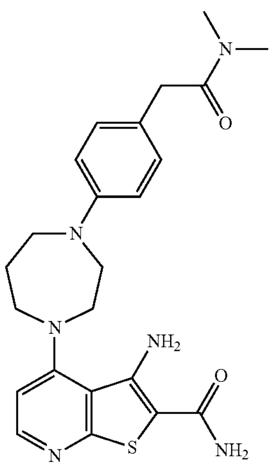 [SMILES: CN(C)C(=O)Cc1ccc(N2CCCN(c3ccnc4sc(C(N)=O)c(N)c34)CC2)cc1] | 0.025 | 82 |
| DBA-8 | 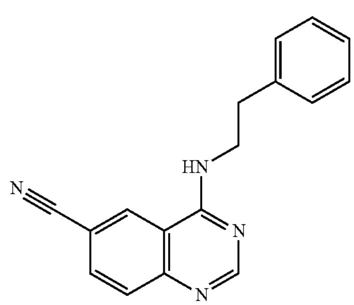 [SMILES: N#Cc1ccc2ncnc(NCCc3ccccc3)c2c1] | 0.5 | 80 |

TABLE 1-continued

| Compound name | Structure | EC$_{50}$ (μM) | EC$_{MAX}$ (% rescue) |
|---|---|---|---|
| DBA-9 | 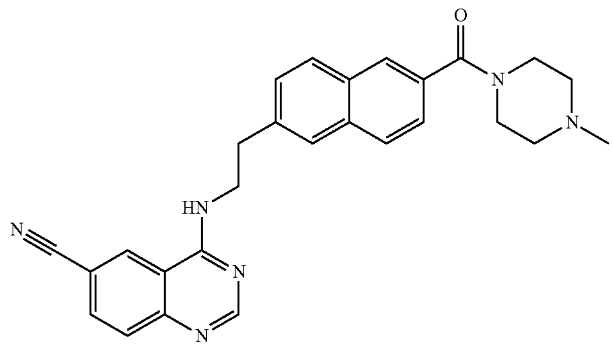 [SMILES: CN1CCN(C(=O)c2ccc3cc(CCNc4ncnc5ccc(C#N)cc45)ccc3c2)CC1] | 0.05 | 60 |
| DBA-10 | 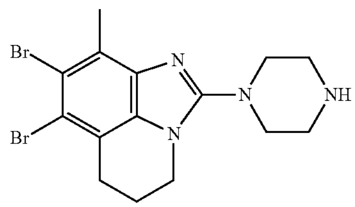 [SMILES: Cc1c(Br)c(Br)c2c3c1nc(N1CCNCC1)n3CCC2] | 0.02 | 60 |
| DBA-11 | 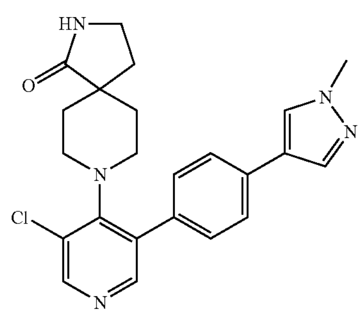 [SMILES: Cn1cc(-c2ccc(-c3cncc(Cl)c3N3CCC4(CCNC4=O)CC3)cc2)cn1] | 0.02 | 50 |
| DBA-12 | 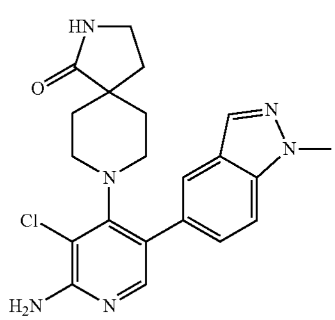 [SMILES: Cn1ncc2cc(-c3cnc(N)c(Cl)c3N3CCC4(CCNC4=O)CC3)ccc21] | N/A | N/A |

CDK8 and/or CDK19 Inhibitors of Formula (I)

In one embodiment, the CDK8 and/or CDK19 inhibitor for use according to the present invention is a compound of the general formula (I), or a prodrug, tautomer or pharmacologically acceptable salt thereof:

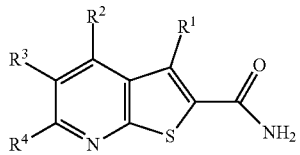

Formula (I)

wherein:

$R^1$ is selected from the group consisting of a hydrogen atom, $C_1$-$C_6$ alkyl, —$NH_2$, alkyl-amine, $R^2$ is selected from the group consisting of a hydrogen atom, —$N(CH_3)_2$, —$NH_2$, methyl, trifluoromethyl, —$CH_2OCH_3$, -$PhOCH_3$, -$PhCH_3$, -PhCl or a group of any one of the formulas (II), (III), (IV) and (V):

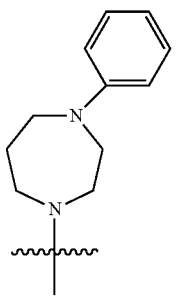

Formula (II)

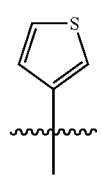

Formula (III)

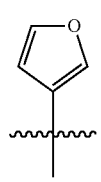

Formula (IV)

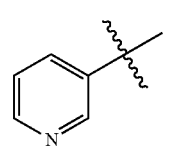

Formula (V)

$R^3$ is selected from the group consisting of a hydrogen atom, methyl, acetyl, phenyl, cyclopropyl, and a group of the formula (V):

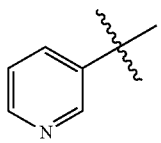

Formula (V)

$R^4$ is selected from the group consisting of a hydrogen atom, methyl, ethyl, cyclopropyl, $C_1$-$C_6$ alkyl, acetyl, phenyl, trifluoromethyl, —$CH_2CH(CH_3)_2$, -PhCl, -$PhCH_3$ or a group of the formulas (III) or (VII):

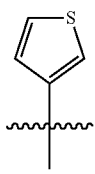

Formula (III)

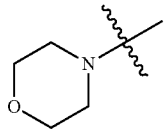

Formula (VII)

or wherein $R^4$ is an oxygen atom double bonded to the carbon atom of the thienopyridine ring thus forming a structure of formula (VI):

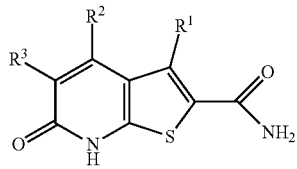

Formula (VI)

or wherein $R^2$ and $R^3$ are joined to form a 6-membered cyclic structure of the formula (VIII):

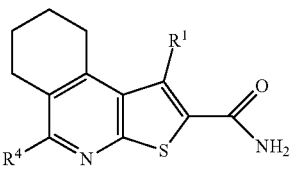

Formula (VIII)

or wherein $R^3$ and $R^4$ are joined to form a 5-, 6- or 7-membered cyclic structure of any one of the formulas (IX), (X), (XI) or (XII):

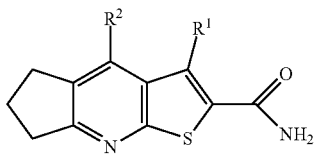

Formula (IX)

-continued

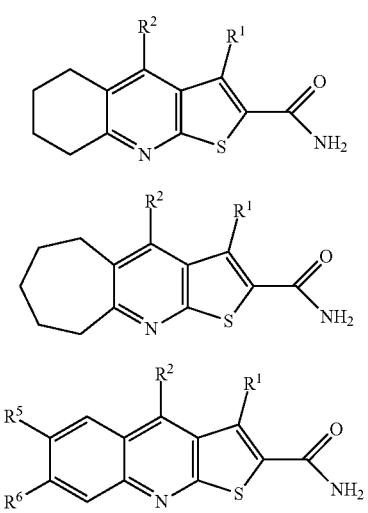

Formula (X)

Formula (XI)

Formula (XII)

wherein $R^5$ and $R^6$ optionally and individually are —OCH$_3$.

The CDK8 and/or CDK19 inhibitor may in one embodiment be a compound of the general formula (I), or a salt, prodrug, tautomer or pharmacologically acceptable salt thereof:

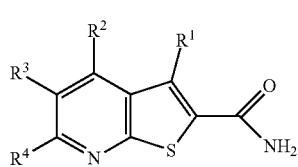

Formula (I)

wherein:
$R^1$ is —NH$_2$;
$R^2$ represents $R^aS$—, $R^aO$—, $R^aNH$—, $R^a(R^b)N$— or a group of formula (XIII):

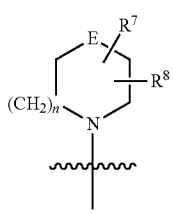

Formula (XIII)

wherein $R^a$ and $R^b$ are the same or different and independently represent a $C_1$-$C_6$ alkyl group which may be substituted with one or more groups selected from Substituent Group α and Substituent Group γ; a $C_3$-$C_8$ cycloalkyl group which may be substituted with one or more groups selected from Substituent Group α, Substituent Group β and Substituent Group γ; a 5- to 7-membered heterocyclyl group which may be substituted with one or more groups selected from Substituent Group α, Substituent Group β and Substituent Group γ and which contains 1 to 3 sulfur, oxygen and/or nitrogen atoms; a $C_6$-$C_{10}$ aryl group which may be substituted with one or more groups selected from Substituent Group α, Substituent Group β and Substituent Group γ; or a 5- to 7-membered heteroaryl group which may be substituted with one or more groups selected from Substituent Group α, Substituent Group β and Substituent Group γ and which contains 1 to 3 sulfur, oxygen and/or nitrogen atoms, $R^7$ and $R^8$ are the same or different and independently represent a hydrogen atom; a group selected from Substituent Group α, Substituent Group β and Substituent Group γ; a $C_1$-$C_6$ alkyl group substituted with one or more groups selected from Substituent Group γ; or a $C_1$-$C_6$ alkoxy group substituted with one or more groups selected from Substituent Group γ, or when $R^7$ and $R^8$ are bonded to adjacent carbon atoms, $R^7$ and $R^8$ together with the carbon atoms to which they are bonded may form a $C_3$-$C_8$ cycloalkyl group which may be substituted with one or more groups selected from Substituent Group α, Substituent Group β and Substituent Group γ; a 5- to 7-membered heterocyclyl group which may be substituted with one or more groups selected from Substituent Group α, Substituent Group β and Substituent Group γ and which contains 1 to 3 sulfur, oxygen and/or nitrogen atoms; a $C_6$-$C_{10}$ aryl group which may be substituted with one or more groups selected from Substituent Group α, Substituent Group β and Substituent Group γ; or a 5- to 7-membered heteroaryl group which may be substituted with one or more groups selected from Substituent Group α, Substituent Group β and Substituent Group γ and which contains 1 to 3 sulfur, oxygen and/or nitrogen atoms, E represents a single bond; a double bond; an oxygen atom; a sulfur atom; sulfinyl; sulfonyl; or a group having the formula $R_9N<$;

$R_9$ represents a hydrogen atom; a $C_1$-$C_6$ alkyl group which may be substituted with one or more groups selected from Substituent Group α and Substituent Group γ; a $C_2$-$C_6$ alkenyl group which may be substituted with one or more groups selected from Substituent Group α and Substituent Group γ; a $C_3$-$C_8$ cycloalkyl group which may be substituted with one or more groups selected from Substituent Group α, Substituent Group β and Substituent Group γ; a 5- to 7-membered heterocyclyl group which may be substituted with one or more groups selected from Substituent Group α, Substituent Group β and Substituent Group γ and which contains 1 to 3 sulfur, oxygen and/or nitrogen atoms; a $C_6$-$C_{10}$ aryl group which may be substituted with one or more groups selected from Substituent Group α, Substituent Group β and Substituent Group γ; a 5- to 7-membered heteroaryl group which may be substituted with one or more groups selected from Substituent Group α, Substituent Group β and Substituent Group γ and which contains 1 to 3 sulfur, oxygen and/or nitrogen atoms; a formyl group; a $C_2$-$C_7$ alkylcarbonyl group which may be substituted with one or more groups selected from Substituent Group α and Substituent Group γ; a 5- to 7-membered heterocyclylcarbonyl group which may be substituted with one or more groups selected from Substituent Group α, Substituent Group β and Substituent Group γ and which contains 1 to 3 sulfur, oxygen and/or nitrogen atoms; a $C_7$-$C_{11}$ arylcarbonyl group which may be substituted with one or more groups selected from Substituent Group α, Substituent Group β and Substituent Group γ; a 5- to 7-membered heteroarylcarbonyl group which may be substituted with one or more groups selected from Substituent Group α, Substituent Group β and Substituent Group γ and which contains 1 to 3 sulfur, oxygen and/or nitrogen atoms; a $C_1$-$C_6$ alkylsulfonyl group which may be substituted with one or more groups selected from Substituent Group α and Substituent Group γ; a $C_6$-$C_{10}$ arylsulfonyl group which may be substituted with one or more groups selected from Substituent Group α, Substituent Group β and Substituent Group γ; a 5- to 7-membered heteroarylsulfonyl group which may be substituted with one or more groups selected from Substituent Group α, Substituent Group β and Substituent Group γ and which contains 1 to 3 sulfur, oxygen and/or nitrogen atoms; a $C_2$-$C_7$ alkoxycarbonyl group which may be substituted with one or more groups selected from Substituent Group α and Substituent Group γ; a $C_7$-$C_{11}$ aryloxycarbonyl group which may be substituted with one or more groups selected from Substituent Group α, Substituent Group β and Substituent Group γ; or a group having the formula $R^c(R^d)N-CO-$ (wherein $R^c$ and $R^d$ are the same or different and independently represent a hydrogen atom or a $C_1$-$C_6$ alkyl group which may be substituted with one or more groups selected from Substituent Group α and Substituent Group γ), n represents an integer of 1 to 4, Substituent Group α represents the group consisting of a halogen atom; a nitro group; a cyano group; a hydroxy group; a group having the formula $R^{10}-CO-$, the formula $R^e(R^f)N-$, the formula $R^e(R^f)N-CO-$ or the formula $R^e(R^f)N-SO_2-$ (wherein $R^{10}$ represents a hydrogen atom, a $C_1$-$C_6$ alkyl group, a $C_1$-$C_6$ halogenated alkyl group, a $C_3$-$C_8$ cycloalkyl group, a hydroxy group, a $C_1$-$C_6$ alkoxy group, a $C_6$-$C_{10}$ aryl group or a $C_6$-$C_{10}$ aryloxy group and $R^e$ and $R^f$ are the same or different and independently represent a hydrogen atom; a $C_1$-$C_6$ alkyl group; a $C_1$-$C_6$ alkoxy group; a $C_6$-$C_{10}$ aryl group; a 5- to 7-membered heteroaryl group which contains 1 to 3 sulfur, oxygen and/or nitrogen atoms; a formyl group; a $C_2$-$C_7$ alkylcarbonyl group; a $C_2$-$C_7$ alkoxycarbonyl group; a $C_7$-$C_{11}$ arylcarbonyl group; a 5- to 7-membered heteroarylcarbonyl group which contains 1 to 3 sulfur, oxygen and/or nitrogen atoms; a $C_1$-$C_6$ alkylsulfonyl group; a $C_6$-$C_{10}$ arylsulfonyl group; or a 5- to 7-membered heteroarylsulfonyl group which contains 1 to 3 sulfur, oxygen and/or nitrogen atoms, or alternatively $R^e$ and $R^f$ together with the nitrogen atom to which they are bonded form a 4- to 7-membered heterocyclyl group which contains 1 to 3 sulfur, oxygen and/or nitrogen atoms (wherein the heterocyclyl group may have 1 or 2 substituent groups selected from a hydroxy group and a methyl group)); a hydroxyimino group; a $C_1$-$C_6$ alkoxyimino group; a $C_1$-$C_6$ alkoxy group; a $C_3$-$C_8$ cycloalkyloxy group; a $C_1$-$C_6$ halogenated alkoxy group; a $C_1$-$C_6$ alkylthio group; a $C_1$-$C_6$ alkylsulfinyl group; and a $C_1$-$C_6$ alkylsulfonyl group, Substituent Group β represents the group consisting of a $C_1$-$C_6$ alkyl group which may be substituted with one or more groups selected from Substituent Group α; and a $C_1$-$C_6$ alkyl group substituted with a 5- to 7-membered heterocyclyl group which may be substituted with one or more groups selected from Substituent Group α, and a $C_1$-$C_6$ alkyl group and which contains 1 to 3 sulfur, oxygen and/or nitrogen atoms, and Substituent Group γ represents the group consisting of a $C_1$-$C_6$ alkoxy group substituted with one or more groups selected from Substituent Group α; a $C_1$-$C_6$ alkylthio group substituted with one or more groups selected from Substituent Group α; a $C_3$-$C_8$ cycloalkyl group which may be substituted with one or more groups selected from Substituent Group α and Substituent Group β; a 5- to 7-membered heterocyclyl group which may be substituted with one or more groups selected from Substituent Group α and Substituent Group β and which contains 1 to 3 sulfur, oxygen and/or nitrogen atoms; a $C_6$-$C_{10}$ aryl group which may be substituted with one or more groups selected from Substituent Group α and Substituent Group β; a 5- to 7-membered heteroaryl group which may be substituted with one or more groups selected from Substituent Group α and Substituent Group β and which contains 1 to 3 sulfur, oxygen and/or nitrogen atoms; a $C_3$-$C_8$ cycloalkyloxy group which may be substituted with one or more groups selected from Substituent Group α and Substituent Group β a 5- to 7-membered heterocyclyloxy group which may be substituted with one or more groups selected from Substituent Group α and Substituent Group β and which contains 1 to 3 sulfur, oxygen and/or nitrogen atoms; a $C_6$-$C_{10}$ aryloxy group which may be substituted with one or more groups selected from Substituent Group α and Substituent Group β; a 5- to 7-membered heteroaryloxy group which may be substituted with one or more groups selected from Substituent Group α and Substituent Group β and which contains 1 to 3 sulfur, oxygen and/or nitrogen atoms; and a $C_6$-$C_{10}$ aryl-$C_1$-$C_6$ alkoxy group in which the aryl moiety may be substituted with one or more groups selected from Substituent Group α and Substituent Group β or a pharmacologically acceptable salt thereof;

$R^3$ is a hydrogen atom; and $R^4$ is selected from the group consisting of a hydrogen atom, a cyclopropyl group or a $C_1$-$C_6$ alkyl group.

In one embodiment $R^4$ is selected from the group consisting of a hydrogen atom, a cyclopropyl group or a $C_1$-$C_4$ alkyl group.

In one embodiment $R^4$ is selected from the group consisting of a hydrogen atom, methyl, ethyl, propyl or cyclopropyl.

In one embodiment $R^4$ is selected from the group consisting of a hydrogen atom or methyl.

In one embodiment $R^2$ is a group consisting of $R^a(R^b)N-$, and $R^a$ and $R^b$ are the same or different and independently represent a $C_1$-$C_6$ alkyl group which may be substituted with one or more groups selected from Substituent Group α and Substituent Group γ.

In one embodiment $R^a$ is a $C_1$-$C_6$ alkyl group which may be substituted with one group selected from Substituent Group α and Substituent Group γ, $R^b$ is a $C_1$-$C_6$ alkyl group, and Substituent Group α is the group consisting of a $C_1$-$C_6$ alkoxy group, and Substituent Group γ is the group consisting of a $C_1$-$C_6$ alkoxy group substituted with one or more groups selected from Substituent Group α; a $C_6$-$C_{10}$ aryloxy group which may be substituted with one or more groups selected from Substituent Group α and Substituent Group β; and a 5- to 7-membered heteroaryloxy group which may be substituted with one or more groups selected from Substituent Group α and Substituent Group β and which contains 1 to 3 sulfur, oxygen and/or nitrogen atoms.

In one embodiment R² is a group of formula (XIII):

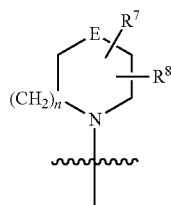

Formula (XIII)

wherein R⁸ is a hydrogen atom or together with R⁷ forms a C₃-C₈ cycloalkyl group which may be substituted with one or more groups selected from Substituent Group α, Substituent Group β and Substituent Group γ; a 5- to 7-membered heterocyclyl group which may be substituted with one or more groups selected from Substituent Group α, Substituent Group β and Substituent Group γ and which contains 1 to 3 sulfur, oxygen and/or nitrogen atoms; a C₆-C₁₀ aryl group which may be substituted with one or more groups selected from Substituent Group α, Substituent Group β and Substituent Group γ; or a 5- to 7-membered heteroaryl group which may be substituted with one or more groups selected from Substituent Group α, Substituent Group β and Substituent Group γ and which contains 1 to 3 sulfur, oxygen and/or nitrogen atoms.

In one embodiment R² is a group of formula (XIII):

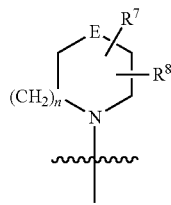

Formula (XIII)

wherein E represents a single bond, an oxygen atom, a sulfur atom or a group having the formula R¹¹N<, wherein R¹¹ represents a C₆-C₁₀ aryl group which may be substituted with one or more groups selected from Substituent Group α, Substituent Group β and Substituent Group γ; a 5- to 7-membered heteroaryl group which may be substituted with one or more groups selected from Substituent Group α, Substituent Group β and Substituent Group γ and which contains 1 to 3 sulfur, oxygen and/or nitrogen atoms; a formyl group; a C₂-C₇ alkylcarbonyl group which may be substituted with one or more groups selected from Substituent Group α and Substituent Group γ; a C₁-C₆ alkylsulfonyl group which may be substituted with one or more groups selected from Substituent Group α and Substituent Group γ; a C₆—C₁₀ arylsulfonyl group which may be substituted with one or more groups selected from Substituent Group α, Substituent Group β and Substituent Group γ; a 5- to 7-membered heteroarylsulfonyl group which may be substituted with one or more groups selected from Substituent Group α, Substituent Group β and Substituent Group γ and which contains 1 to 3 sulfur, oxygen and/or nitrogen atoms; a C₂-C₇ alkoxycarbonyl group which may be substituted with one or more groups selected from Substituent Group α and Substituent Group γ; or a group having the formula Rᶜ(Rᵈ)N—CO—, and n is an integer of 1 to 3.

In one embodiment R⁷ is a C₁-C₆ alkoxy group; a C₁-C₆ alkyl group which may be substituted with one or more groups selected from Substituent Group α; a C₁-C₆ alkoxy group substituted with one or more groups selected from Substituent Group α; a C₆-C₁₀ aryloxy group which may be substituted with one or more groups selected from Substituent Group α, Substituent Group β and Substituent Group γ; a C₁-C₆ alkyl group substituted with one or more groups selected from Substituent Group γ; or a C₁-C₆ alkoxy group substituted with one or more groups selected from Substituent Group γ, E is a single bond, and n is an integer 2.

In one embodiment R⁷ is a hydrogen atom, Z is a sulfur atom, and n is 1.

In one embodiment R⁷ is a hydrogen atom, E is a group having the formula R¹¹N<, wherein R¹¹ represents a C₆-C₁₀ aryl group which may be substituted with one or more groups selected from Substituent Group α, Substituent Group β and Substituent Group γ; or a 5- to 7-membered heteroaryl group which may be substituted with one or more groups selected from Substituent Group α, Substituent Group β and Substituent Group γ and which contains 1 to 3 sulfur, oxygen and/or nitrogen atoms; and wherein n is an integer 2.

In a preferred embodiment of the invention the CDK8 and/or CDK19 inhibitor of formula (I) is selected from the group consisting of:

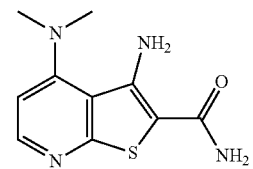

DBA-1

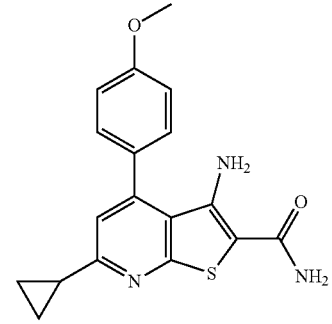

DBA-2

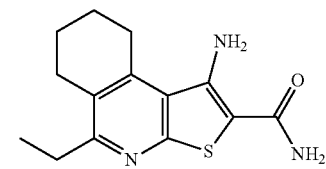

DBA-3

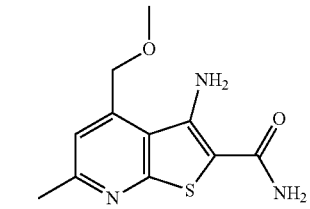

DBA-4

-continued

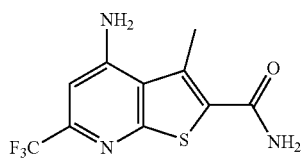
DBA-5

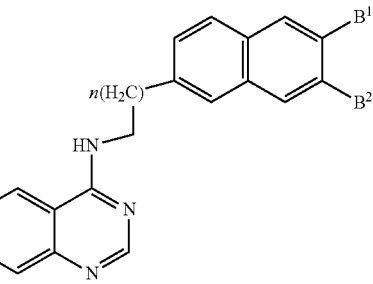
Formula (XV)

wherein B$^1$ is hydrogen when B$_2$ is a group of the formula (XVI); or
wherein B$^2$ is hydrogen when B$^1$ is a group of the formula (XVI):

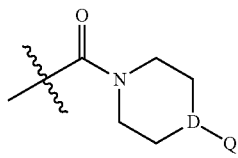
Formula (XVI)

wherein D is selected from C, O, and N; and wherein D is optionally substituted with a group Q wherein Q is selected from hydrogen, —C$_1$-C$_6$-alkyl, —C$_1$-C$_6$-alkoxy-C$_1$-C$_6$-alkyl, —C$_1$-C$_6$-alkylamine; and
n is an integer 0, 1 or 2.

In one embodiment said alkyl is methyl.
In embodiment n is 0 or 1, in particular n may be 1.
In particular, the CDK8 and/or CDK19 inhibitor of formula (XIV) or formula (X) may be a compound selected from the group consisting of DBA-8 and DBA-9:

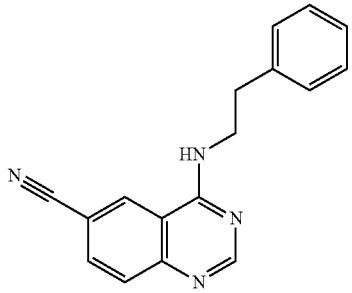
DBA-8

DBA-6

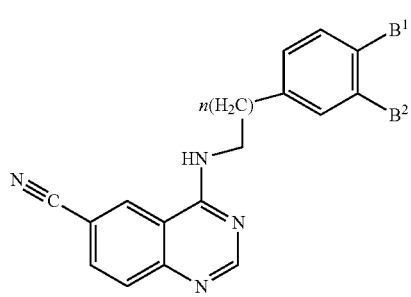
DBA-7

CDK8 and/or CDK19 Inhibitors of Formula (XIV) or (XV)

In one embodiment, the CDK8 and/or CDK19 inhibitor for use according to the present invention is a compound of the general formula (XIV) or (XV), or a prodrug, tautomer or pharmacologically acceptable salt thereof:

Formula (XIV)

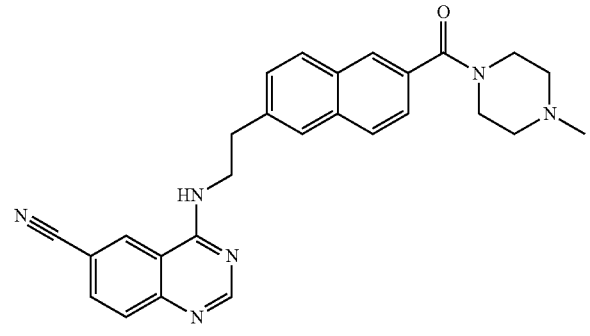
DBA-9

CDK8 and/or CDK19 Inhibitors of Formula (XVII)

In one embodiment, the CDK8 and/or CDK19 inhibitor for use according to the present invention is a compound of the general formula (XVII), or a prodrug, tautomer or pharmacologically acceptable salt thereof:

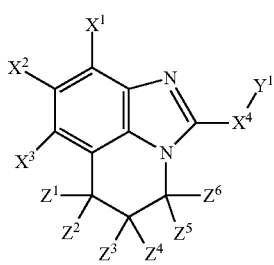

Formula (XVII)

wherein $X^1$, $X^2$ and $X^3$ are each independently selected from the group consisting of H, F, Cl, Br, I, —$OT^1$, —$N(T^2)(T^3)$, —$NHC(=O)T^4$, nitro, cyano, cyclopropyl and —$C_1$-$C_3$ alkyl, with the proviso that at least two substituents selected from $X^1$, $X^2$ and $X^3$ are each independently selected from the group consisting of F, Cl, Br and I;

$Z^1$ and $Z^2$ are each independently selected from the group consisting of H, —$C_1$-$C_6$ alkyl, —$OT^1$ and —$N(T^2)(T^3)$;

$Z^3$ and $Z^4$ are either taken together to form an oxo group at the carbon atom to which they are attached; or $Z^3$ and $Z^4$ are each independently selected from the group consisting of H, —$C_1$-$C_6$ alkyl, —$OT^1$ and —$N(T^2)(T^3)$;

$Z^5$ and $Z^6$ are either taken together to form an oxo group at the carbon atom to which they are attached; or $Z^5$ and $Z^6$ are each independently selected from the group consisting of H, —$C_1$-$C_6$ alkyl, —$OT^1$ and —$N(T^2)(T^3)$;

$X^4$ is either absent or selected from the group consisting of —$NR^{12}$—, —$N(R^{12})(CH_2)$—, —$C(=O)NH$— and —$C(=O)$—; wherein $R^{12}$ is selected from H and —$C_1$-$C_6$ alkyl;

$Y^1$ is selected from the group consisting of H, —$C_1$-$C_6$ alkyl and a 4- to 7-membered saturated or unsaturated aromatic carbocycle or heterocycle, with the proviso that the point of attachment on said heterocycle is carbon if $X^4$ is —$NR^{12}$— or —$C(=O)NH$—, wherein said —$C_1$-$C_6$ alkyl is optionally substituted with one or more substituents independently selected from —$OT^1$, —$ST^1$, —$N(T^2)(T^3)$ and a 5- to 6-membered saturated heterocycle, and wherein said 4- to 7-membered saturated or unsaturated aromatic carbocycle or heterocycle is optionally substituted with one or more substituents independently selected from F, Cl, Br, I, —$C(=O)H$, —$OT^1$, —$N(T^2)(T^3)$, —$C(=O)N(T^2)(T^3)$, —$C(=O)OT^1$, —$ST^1$ and —$C_1$-$C_3$ alkyl, wherein said —$C_1$-$C_3$ alkyl is optionally substituted with one or more substituents independently selected from —$OT^1$ and —$N(T^2)(T^3)$;

$T^1$, $T^2$ and $T^3$ are each independently selected from H and —$C_1$-$C_6$ alkyl optionally substituted with one or more substituents independently selected from —$N(T^5)(T^6)$, —$OT^7$, —$ST^7$, nitro, cyano, —$C(=O)OT^7$, —$C(=O)N(T^5)(T^6)$, —$OC(=O)N(T^5)(T^6)$, —$S(=O)_2T^8$, —$S(=O)_2OT^7$ and —$S(=O)_2N(T^5)(T^6)$;

$T^4$ is —$C_1$-$C_6$ alkyl optionally substituted with one or more substituents independently selected from —$N(T^5)(T^6)$, —$OT^7$, —$ST^7$, nitro, cyano, —$C(=O)OT^7$, —$C(=O)N(T^5)(T^6)$, —$OC(=O)N(T^5)(T^6)$, —$S(=O)_2T^8$, —$S(=O)_2OT^7$ and —$S(=O)_2N(T^5)(T^6)$;

$T^5$, $T^6$ and $T^7$ are each independently selected from H and —$C_1$-$C_6$ alkyl optionally substituted with one or more substituents independently selected from amino, hydroxyl, thiol, nitro and cyano; and $T^8$ is selected from —$C_1$-$C_6$ alkyl optionally substituted with one or more substituents independently selected from amino, hydroxyl, thiol, nitro and cyano;

or a pharmaceutically acceptable salt thereof.

In one embodiment $X^1$ may be selected from the group consisting of H, F, Cl, Br, I, —$OT^1$, —$N(T^2)(T^3)$, —$NHC(=O)T^4$, nitro, cyano, cyclopropyl and —$C_1$-$C_3$ alkyl; and $X^2$ and $X^3$ are independently selected from the group consisting of F, Cl, Br and I.

In one embodiment $Y^1$ may be a 4- to 7-membered saturated or unsaturated carbocycle or heterocycle, with the proviso that the point of attachment on said heterocycle is carbon if $X^4$ is —$NR^{12}$— or —$C(=O)NH$—, wherein said 4- to 7-membered saturated or unsaturated carbocycle or heterocycle is optionally substituted with one or more substituents independently selected from F, Cl, Br, I, —$C(=O)H$, —$OT^1$, —$N(T^2)(T^3)$, —$C(=O)N(T^2)(T^3)$, —$ST^1$ and —$C_1$-$C_3$ alkyl, wherein said —$C_1$-$C_3$ alkyl is optionally substituted with one or more substituents independently selected from —$OT^1$ and —$N(T^2)(T^3)$.

In one embodiment $X^4$ is absent and $Y^1$ is a 4- to 7-membered saturated heterocycle, wherein said 4- to 7-membered saturated heterocycle is optionally substituted with one or more substituents independently selected from F, Cl, Br, I, —$C(=O)H$, —$OT^1$, —$N(T^2)(T^3)$, —$C(=O)N(T^2)(T^3)$, —$C(=O)OT^1$, —$ST^1$ and —$C_1$-$C_3$ alkyl, wherein said —$C_1$-$C_3$ alkyl is optionally substituted with one or more substituents independently selected from —$OT^1$ and —$N(T^2)(T^3)$.

In one embodiment $X^4$ is absent and $Y^1$ is piperazine, wherein said piperazine is optionally substituted with one or more substituents independently selected from F, Cl, Br, I, —$C(=O)H$, —$OT^1$, —$N(T^2)(T^3)$, —$ST^1$ and —$C_1$-$C_3$ alkyl, wherein said —$C_1$-$C_3$ alkyl is optionally substituted with one or more substituents independently selected from —$OT^1$ and —$N(T^2)(T^3)$.

In one embodiment $Z^1$, $Z^2$, $Z^3$, $Z^4$, $Z^5$ and $Z^6$ are each independently selected from the group consisting of H, —$C_1$-$C_6$ alkyl, —$OT^1$ and —$N(T^2)(T^3)$.

In one embodiment the CDK8 and/or CDK19 inhibitor of formula (XVII) is a compound of the formula:

In one embodiment the CDK8 and/or CDK19 inhibitor of formula (XVII) is a compound of the formula:

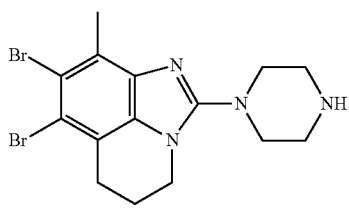

DBA-10

In one embodiment of the invention the CDK8 and/or CDK19 inhibitor of formula (XVII) is 7,8-dibromo-9-methyl-2-(piperazin-1-yl)-5,6-dihydro-4H-imidazo[4,5,1-ij]quinoline hydrochloride.

CDK8 and/or CDK19 Inhibitors of Formula (XVIII)

In one embodiment, the CDK8 and/or CDK19 inhibitor for use according to the present invention is a compound of the general formula (XVIII), or a prodrug, tautomer or pharmacologically acceptable salt thereof:

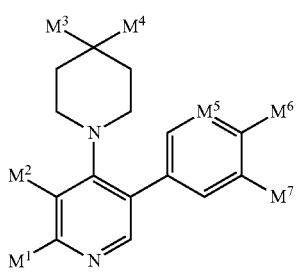

Formula (XVIII)

wherein:
$M^1$ is H or $NH_2$,
$M^2$ is LA, Hal, CN,
$M^3$ is H, Hal, $NH_2$, LA, HO(LA)-, NH(LA),
$M^4$ is CN, $CONH_2$, CONH(LA)
or
$M^3$, $M^4$ together with the C atom they are attached to, form a 5- or 6-membered non-aromatic heterocycle, having 1-3 heteroatoms, individually selected from the group consisting of O, S and N, which is substituted by 1 or 2 oxo groups, which heterocycle may further be monosubstituted by LA or OH, and which heterocycle may form a condensed ring system with a phenyl or pyridyl group,
$M^5$ is CH or N,
$M^6$ is Cyc, CON $H_2$, COO(LA) or CONH(LA),
$M^7$ is H,
or
$M^6$, $M^7$ together with the atoms they are attached to, form a 5- or 6-membered heterocycle, having 1-3 heteroatoms, individually selected from the group consisting of O, S and N, which is, optionally, independently mono- di- or trisubstituted by oxo, OH, LA, $NH_2$, NH(LA), $N(LA)_2$) NHCOO(LA) or HO(LA)-,
Cyc is a 5- or 6-membered monocyclic, aliphatic or aromatic homo- or heterocycle having 1-3 heteroatoms, individually selected from the group consisting of O, S and N, which may be mono- or di-substituted by oxo, LA, $NH_2$, NH(LA), $N(LA)_2$, HO(LA)-, or monosubstituted by CA,
LA is an unbranched or branched alkyl, having 1, 2, 3, 4 or 5 carbon atoms, which may be saturated or partially unsaturated, wherein 1, 2 or 3 H atoms may be replaced by Hal, and/or
1 $CH_3$ group may be replaced by CN, or
1 $CH_2$ group may be replaced by —O—, —NH— or —$SO_2$—, and/or
1 CH group may be replaced by N,
CA is a cycloalkyl having 3, 4, 5 or 6 carbon atoms, cycloalkyl alkyl having 3, 4, 5 or 6 ring carbon atoms and 1 or 2 non-ring carbon atoms, in which cycloalkyl or cycloalkyl alkyl one ring atom may be replaced by O, and which cycloalkyl or cycloalkyl alkyl may be monosubstituted by OH,
Hal is F, Cl, Br or I.

In one embodiment, the CDK8 and/or CDK19 inhibitor for use according to the present invention is a compound of the general formula (XIX), or a prodrug, tautomer or pharmacologically acceptable salt thereof:

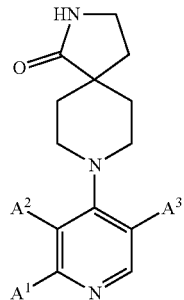

Formula (XIX)

wherein:
$A^1$ is selected from the group consisting of a hydrogen atom and —$NH_2$,
$A^2$ is selected from the group consisting of —Cl, —F, —Br, —I and a hydrogen atom,
$A^3$ is selected from the group of formulas (XX) and (XXI);

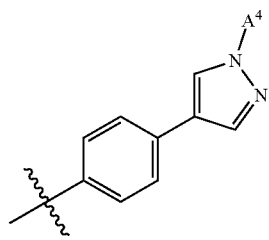

Formula (XX)

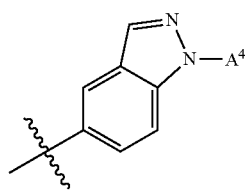

Formula (XXI)

wherein:
$A^4$ is a hydrogen atom or a $C_1$-$C_6$ alkyl of which one or more atoms may individually be replaced with an atom selected from the group consisting of O, N, and S, and which may be substituted with one or more groups individually selected from the group consisting of $C_1$-$C_5$ alkyl, —OH, oxo, and —$NA^5A^6$, wherein $A^5$ and $A^6$ are individually selected from the group consisting of hydrogen and $C_1$-$C_6$ alkyl that may be joined to form a 3-, 4-5- or 6-membered cyclic structure, In one embodiment, $A^2$ is —Cl.

In one embodiment $A^4$ is —$CH_3$.

In particular, the CDK8 and/or CDK19 inhibitor of formula (XVIII) or formula (XIX) is a compound of the formula:

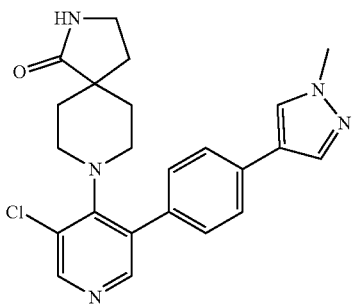

DBA-11

In particular, the CDK8 and/or CDK19 inhibitor of formula (XVIII) or formula (XIX) is 8-[3-chloro-5-[4-(1-methyl-1H-pyrazol-4-yl)phenyl]-4-pyridinyl]-2,8-diazaspiro[4.5]decan-1-one.

In particular, the CDK8 and/or CDK19 inhibitor of formula (XVIII) or formula (XIX) is a compound of the formula:

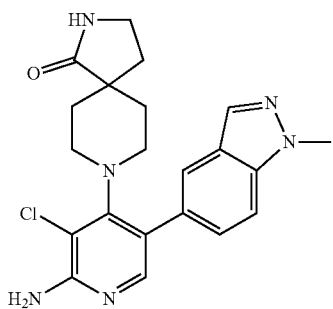

DBA-12

In particular, the CDK8 and/or CDK19 inhibitor of formula (XVIII) or formula (XIX) is 8-(2-Amino-3-chloro-5-(1-methyl-1H-indazol-5-yl)pyridin-4-yl)-2,8-diazaspiro[4.5]decan-1-one.

Salts, Prodrugs, Solvates and Tautomers

As mentioned herein above the CDK8 and/or CDK19 inhibitor may be any of the compounds of formula (I), formula (XIV), formula (XV), formula (XVII) or formula (XVIII) described herein above or prodrugs, tautomers or pharmacologically acceptable salts thereof.

Said pharmacologically acceptable salt may be any salts, such as acid or base additions salts of the CDK8 and/or CDK19 inhibitors of the present invention which are, within the scope of sound medical judgment, suitable for use without undue toxicity, irritation, allergic response, and the like, commensurate with a reasonable benefit/risk ratio, and effective for their intended use, as well as the zwitterionic forms, where possible, of the compounds of the invention.

Pharmacologically acceptable salts refers to the relatively non-toxic, inorganic and organic addition salts of CDK8 and/or CDK19 inhibitors of the present invention. These salts can be prepared in situ during the final isolation and purification of the compounds, or by subsequently reacting the purified compound in its free acid or base form with a suitable organic or inorganic compound and isolating the salt thus formed.

In so far as the CDK8 and/or CDK19 inhibitors of this invention are basic compounds, they are all capable of forming a wide variety of different salts with various inorganic and organic acids. Although such salts must be pharmacologically acceptable for administration to animals, it is often desirable in practice to initially isolate the compound from the reaction mixture as a pharmaceutically unacceptable salt and then simply convert to the free base compound by treatment with an alkaline reagent and thereafter convert the free base to a pharmaceutically acceptable acid addition salt.

The compounds of the present invention may exist in unsolvated forms as well as in solvated forms, including hydrated forms. In general, the solvated forms, including hydrated forms, are equivalent to unsolvated forms and are intended to be encompassed within the scope of the present invention.

The term "prodrug" refers to compounds that are rapidly transformed in vivo to yield the parent CDK8 and/or CDK19 inhibitors of the above formulae, for example, by hydrolysis. A thorough discussion is provided in T. Higuchi and V Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference. Examples of prodrugs include pharmaceutically acceptable, non-toxic esters of the compounds of the present invention, including $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. $C_1$-$C_4$ alkyl esters are preferred. Esters of the compounds of the present invention may be prepared according to conventional methods "March's Advanced Organic Chemistry, $5^{th}$ Edition". M. B. Smith & J. March, John Wiley & Sons, 2001.

CDK8 and/or CDK19 inhibitors may contain chiral centers and therefore may exist in different enantiomeric and diastereomeric forms. This invention relates to all optical isomers and all stereoisomers of the CDK8 and/or CDK19 inhibitors of formulas (I), XIV), (XV), (XVII) or (XVIII) unless otherwise specified.

Pharmaceutical Formulations

Whilst it is possible for the CDK8 and/or CDK19 inhibitors or salts of the present invention to be administered as the raw chemical, it is preferred to present them in the form of a pharmaceutical formulation. Accordingly, the present invention further provides a pharmaceutical formulation, which comprises a CDK8 and/or CDK19 inhibitors of the present invention or a pharmacologically acceptable salt thereof, as herein defined, and a pharmaceutically acceptable carrier therefor. The pharmaceutical formulations may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavoring agents, solubilizers, lubricants, suspending agents, binders, preservatives, wetting agents, tablet disintegrating agents, or an encapsulating material.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The CDK8 and/or CDK19 inhibitors of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The CDK8 and/or CDK19 inhibitors of the invention may also be formulated for topical delivery. The topical formulation may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example.

Preferably, the formulation will comprise about 0.5% to 75% by weight of the active ingredient(s) with the remainder consisting of suitable pharmaceutical excipients as described herein.

EXAMPLES

Example 1: Phenotypic Assay for Rescued Cell Proliferation of Murine RPS19-Deficient Erythroid Progenitor Cells A previously described screening assay was utilized for identifying Diamond Blackfan Anemia candidate drugs (55$^{th}$ ASH annual meeting, New Orleans, La., Dec. 7-10, 2013; Abstract #2472 by Siva et al.). This robust assay for screening chemical libraries to identify small molecules that rescue the proliferation defect in RPS19-deficient erythroid cells was utilized. Cells used in the assay were primary c-Kit+E14.5-15.5 fetal liver erythroid progenitor cells from a mouse model of DBA with doxycycline inducible expression of rps19-shRNA (Jaako et al. Blood. 2011 Dec. 1; 118(23):6087-96). Correction of reduced proliferative capacity of RPS19-deficient erythroid progenitors was used as readout in a phenotypic screen for novel drug candidates. The hits from the screen included a series of thienopyridines, some of which have previously been described as bone anabolic agents (Saito et al. *Bioorg. Med. Chem.* 2013, 21, 1628-42 and US 2007/0219234). Interestingly, it was found that the potency of the thienopyridines DBA-1, DBA-6 and DBA-7 in the phenotypic assay of rescued proliferation correlated with their potency as bone anabolic agents previously described by Saito et al. (2013).

In addition, our results indicate that these thienopyridines have a novel therapeutic target, i.e. CDK8/CDK19 for rescue of proliferation of erythroid progenitor cells.

Example 2: Thienopyridine Compounds Rescue Proliferation of RPS19-Deficient Erythroid Cells Validation of our screening hits and further testing revealed that DBA-1 and several other thienopyridines including DBA-2, DBA-3, DBA-4, DBA-5, DBA-6 and DBA-7 (see Table 1 above for their structure) were potent in our proliferation rescue assay.

Figure 1:
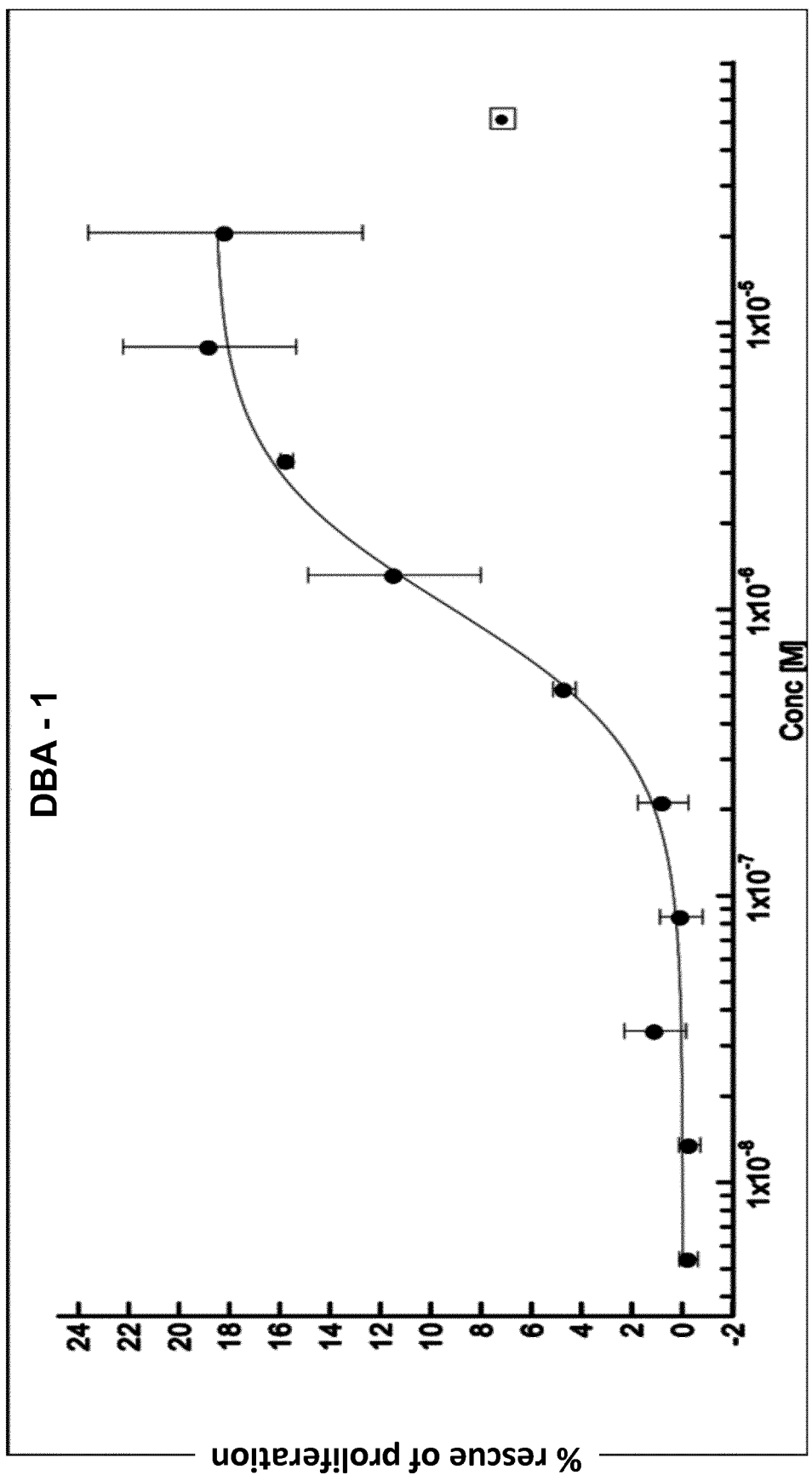
FIG. 1: DBA-1 confers a dose-dependent rescue of proliferation of RPS19-deficient murine erythroid progenitor cells.

FIGS. 1-3 show that DBA-1, DBA-6 and DBA-7 dose-dependently rescue proliferation in our proliferation rescue assay. DBA-1 was found to have a higher $EC_{50}$ value than DBA-6 and DBA-6 was, in turn, found to have a higher $EC_{50}$ value than DBA-7. These results indicate that the therapeutic mechanism in our assay was related to the bone anabolic mechanism of this group of thienopyridines.

Example 3: Kinome Scans of DBA-6 and DBA-7 Show CDK8/CDK19 as Common Kinase Targets After identifying the series of active thienopyridine compounds including DBA-1, DBA-2, DBA-3, DBA-4, DBA-5, DBA-6 and DBA-7, the mechanism by which these compounds rescue proliferation of RPS19-deficient erythroid progenitor cells was investigated.

We hypothesized that the therapeutic mechanism was through inhibition of a kinase and therefore performed KinomeScan at DiscoverEx testing activity on 468 kinases for DBA-6 and DBA-7. While DBA-6 inhibited CDK8 and CDK19 in addition to a limited set of other kinases at 10 µM (data not shown), DBA-7 very selectively inhibited these two kinases at 0.5 µM (FIG. 5). The unusual selectivity of DBA-7 for CDK8 and CDK19 suggested that the therapeutic mechanism of DBA-7 in our proliferation rescue assay as well as in the bone anabolic assay (Saito et al. Bioorg. Med. Chem. 2013, 21, 1628-42) is due to inhibition of CDK8 and/or CDK19.

Example 4: The CDK8/CDK19 Inhibitor DBA-8 Rescues Proliferation of RPS19-Deficient Erythroid Progenitor Cells The results presented in Example 3 and in particular the KinomeScan indicate that the activity of DBA-7 in our proliferation assay was due to inhibition of CDK8 and/or CDK19. Since DBA-4 also inhibited CDK19 (FIG. 4), we hypothesized that CDK8 and/or CDK19 is the common target of the active compounds in the thienopyridine series.

To confirm CDK8 and/or CDK19 as therapeutic targets for rescuing proliferation of RPS19-deficient cells, the activity of structurally different molecules with the same kinase target profile in the proliferation rescue assay was tested. A group of selective CDK8/CDK19 inhibitors were previously described in a paper by Porter et al. (*Nat. Acad. Sci. Proc.* 2012, 109, 13799-13804). Compound DBA-9 (described as Senexin B in WO 2013/116786) has a very similar kinase inhibition profile as DBA-7. We therefore tested the structurally similar and commercially available CDK8/CDK19 inhibitor DBA-8 (described as Senexin A by Porter et al. 2012) in our proliferation rescue assay. As our hypothesis predicted, DBA-8 was capable of rescuing the proliferation defect of RPS19 erythroid progenitor cells in a partially dose-dependent manner (FIG. 6).

In addition, the selective CDK8/CDK19 inhibitors DBA-7 and DBA-8 both rescued RPS19-deficient erythroid progenitor cells from apoptosis (FIG. 7) and loss of kit+ progenitor cell maintenance in culture (FIG. 8).

These results confirm that inhibition of CDK8/CDK19 is the mechanism of action for DBA-6, DBA-7 and DBA-8 and indicate that DBA-9 and other CDK8/CDK19 inhibitors such as DBA-10 (compound 1K described in WO 2014/072435), DBA-11 and DBA-12 can rescue proliferation of RPS19-deficient cells.

Example 5: DBA-9 and/or DBA-10 Rescues Anemia in RPS19-Deficient Mice

To determine if CDK8/CDK19 inhibitors will rescue anemia in RPS19-deficient mice (Jaako et al. Blood. 2011 Dec. 1; 118(23):6087-96) we evaluated the effect of DBA-9 in vivo. 36 hours after Doxycycline induction of RPS19-deficiency mice were given oral doses of 10 mg/kg DBA-9 every 12 hours. Treatment was stopped after 5 doses. 48 hours after last treatment peripheral blood was analysed for reticulocyte counts, which reflects the ongoing production of erythrocytes. Reticulocyte counts were severely reduced in untreated and vehicle treated Rps19-deficient mice, but rescued in RPS19-deficient mice treated with DBA-9 (FIG. 9).

To determine the ability to rescue anemia in RPS19-deficient mice of DBA-10 and other selective CDK8/CDK19 inhibitors, additional in vivo experiments are performed according to the experimental set-up described above in this example RPS19-deficient mice are given oral doses of 10 mg/kg DBA-1, DBA-2, DBA-3, DBA-4, DBA-5, DBA-6, DBA-7, DBA-8, DBA-10, DBA-11 or DBA-12 (see Table 1 for structures) every 12 hours. Treatment is stopped after 5 doses. 48 hours after last treatment peripheral blood is analysed for reticulocyte counts, which reflects the ongoing production of erythrocytes. Reticulocyte counts is rescued in RPS19-deficient mice treated with the selective CDK8/CDK19 inhibitors tested. In addition to rescue of reticulocyte and haemoglobin levels, other effects of the tested CDK8/CDK19 inhibitors are determined, in particular their ability to rescue bone marrow hypocellularity, to promote hemapopoetic stem and progenitor development, as well as cell cycle arrest and apoptosis.

Example 6: DBA-9 and DBA-10 Rescue Erythroid Proliferation and Maturation of Primary DBA Patient Cells To confirm that CDK8/CDK19 inhibitors rescue erythropoiesis also in human DBA patient cells, CD34+ cells were isolated from healthy donors and DBA patients. CD34+ cells were cultured in conditions supporting expansion of erythroid progenitors and precursors. Three CDK8/CDK19 inhibitors and vehicle control were added to the cultures. DBA patient cells expanded poorly compared to healthy donor cells, but gained ability to proliferate in presence of CDK8/CDK19 inhibitors DBA-9 and DBA10 (FIG. 10 and FIG. 11). Compared to healthy cells DBA patient cells failed to mature to CD71+ erythroid progenitor cells and CD71/CD235a double-positive erythroid precursors. DBA patient cells gained ability to mature to erythroid progenitor/precursors in presence of CDK8/CDK19 inhibitors DBA-9 and DBA10 (FIG. 12 and FIG. 13).

These results indicate that CDK8/CDK19 inhibitors rescue erythropoiesis also in human DBA patient cells.

Example 7: DBA-9 and/or DBA-10 are Bone Anabolic Agents

DBA-1, DBA-6 and DBA-7 are known to have an effect as bone anabolic agents. The mechanism of action has however been unknown. The present inventors, for the first time, demonstrate that DBA-7 is a selective CDK8/CDK19 inhibitor, and propose that all selective CDK8/CDK19 inhibitors such as DBA-9 and DBA-10 also have bone anabolic properties. The inventors are evaluating the bone anabolic effects of DBA-9, DBA-10 and other CDK8/CDK19 inhibitors on bone formation as follows. The alkaline phosphatase activity of ST2 cells is utilized as an indicator of osteoblastic differentiation and it is expected that CDK8/CDK19 inhibitors enhance this activity similar to DBA-7 (Saito et al. *Bioorg. Med. Chem.* 2013, 21, 1628-42). To confirm activity on primary cells the effect of CDK8/CDK19 inhibitors on differentiation of primary osteoblasts and osteoclasts are determined. Next the effect of CDK8/CDK19 inhibitors on osteoblastic differentiation and bone remodelling in vivo are determined. Experiments include evaluating the effects on areal bone mineral density in rodent models for osteoporosis (Saito et al. *Bioorg. Med. Chem.* 2013, 21, 1628-42).

Example 8: Assay for Testing CDK8/CDK19 Inhibitory Activity of Candidate Compounds We demonstrate that cell proliferation of RPS19-deficient erythroid cells is improved by specific CDK8/CDK19 inhibitors. A cell-based phenotypic screening assay aiming to identify molecules with positive effect on proliferation of RPS19-deficient erythroid cells is a novel tool for identifying and evaluating novel CDK8/CDK19 inhibitors. One advantage with this screening assay compared to many other high throughput screening assays for identifying CDK8/CDK19 inhibitors is that generally toxic compounds are not identified as hits, thus eliminating many unspecific kinase inhibitors. Cell proliferation in high throughput screens is thus determined by measuring the number of viable RPS19-deficient cells in a well using high throughput imaging or ATP (Niles et al. *Curr Chem Genomics.* 2009, 3, 33-41).

The invention claimed is:

1. A method of treating a clinical condition in an individual in need thereof, comprising
administering to the individual a therapeutically effective amount of an inhibitor of cyclin-dependent kinase 8 (CDK8) and/or cyclin-dependent kinase 19 (CDK19), wherein the clinical condition is a ribosomopathy, and/or a disease characterized by reduced number of hematopoietic stem cells and/or progenitor cells; or
administering to the individual a therapeutically effective amount of an inhibitor of cyclin-dependent kinase 8 (CDK8) and/or cyclin-dependent kinase 19 (CDK19), with the proviso that the inhibitor of CDK8 and/or the inhibitor of CDK19 is not a thienopyridine compound, wherein the clinical condition is a bone anabolic disorder.

2. The method according to claim 1, wherein the inhibitor of CDK8 and/or the inhibitor of CDK19 has the structure of formula (XVII):

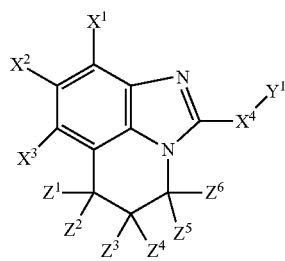

Formula (XVII)

wherein $X^1$, $X^2$ and $X^3$ are each independently selected from the group consisting of H, F, Cl, Br, I, $-OT^1$, $-N(T^2)(T^3)$, $-NHC(=O)T^4$, nitro, cyano, cyclopropyl and —C$_1$-C$_3$ alkyl, with the proviso that at least two substituents selected from X$^1$, X$^2$ and X$^3$ are each independently selected from the group consisting of F, Cl, Br and I;

Z$^1$ and Z$^2$ are each independently selected from the group consisting of H, —C$_1$-C$_6$ alkyl, —OT$^1$ and —N(T$^2$)(T$^3$);

Z$^3$ and Z$^4$ are either taken together to form an oxo group at the carbon atom to which they are attached; or Z$^3$ and Z$^4$ are each independently selected from the group consisting of H, —C$_1$-C$_6$ alkyl, —OT$^1$ and —N(T$^2$)(T$^3$);

Z$^5$ and Z$^6$ are either taken together to form an oxo group at the carbon atom to which they are attached; or Z$^5$ and Z$^6$ are each independently selected from the group consisting of H, —C$_1$-C$_6$ alkyl, —OT$^1$ and —N(T$^2$)(T$^3$);

X$^4$ is either absent or selected from the group consisting of —NR$^{12}$—, —N(R$^{12}$)(CH$_2$)—, —C(=O)NH— and —C(=O)—; wherein R$^{12}$ is selected from H and —C$_1$-C$_6$ alkyl;

Y$^1$ is selected from the group consisting of H, —C$_1$-C$_6$ alkyl and a 4- to 7-membered saturated or unsaturated aromatic carbocycle or heterocycle, with the proviso that the point of attachment on said heterocycle is carbon if X$^4$ is NR$^{12}$— or —C(=O)NH—, wherein said —C$_1$-C$_6$ alkyl is optionally substituted with one or more substituents independently selected from —OT$^1$, —ST$^1$, —N(T$^2$)(T$^3$) and a 5- to 6-membered saturated heterocycle, and wherein said 4- to 7-membered saturated or unsaturated aromatic carbocycle or heterocycle is optionally substituted with one or more substituents independently selected from F, Cl, Br, I, —C(=O)H, —OT$^1$, —N(T$^2$)(T$^3$), —C(=O)N(T$^2$)(T$^3$), —C(=O)OT$^1$, —ST$^1$ and —C$_1$-C$_3$ alkyl, wherein said —C$_1$-C$_3$ alkyl is optionally substituted with one or more substituents independently selected from —OT$^1$ and —N(T$^2$)(T$^3$);

T$^1$, T$^2$ and T$^3$ are each independently selected from H and —C$_1$-C$_6$ alkyl optionally substituted with one or more substituents independently selected from —N(T$^5$)(T$^6$), —OT$^7$, —ST$^7$, nitro, cyano, —C(=O)OT$^7$, —C(=O)N(T$^5$)(T$^6$), —OC(=O)N(T$^5$)(T$^6$), —S(=O)$_2$T$^7$, —S(=O)$_2$OT$^8$ and —S(=O)$_2$N(T$^5$)(T$^6$);

T$^4$ is —C$_1$-C$_6$ alkyl optionally substituted with one or more substituents independently selected from —N(T$^5$)(T$^6$), —OT$^7$, —ST$^7$, nitro, cyano, —C(=O)OT$^7$, —C(=O)N(T$^5$)(T$^6$), —OC(=O)N(T$^5$)(T$^6$), —S(=O)$_2$T$^8$, —S(=O)$_2$OT$^7$ and —S(=O)$_2$N(T$^5$)(T$^6$);

T$^5$, T$^6$ and T$^7$ are each independently selected from H and —C$_1$-C$_6$ alkyl optionally substituted with one or more substituents independently selected from amino, hydroxyl, thiol, nitro and cyano; and T$^8$ is selected from —C$_1$-C$_6$ alkyl optionally substituted with one or more substituents independently selected from amino, hydroxyl, thiol, nitro and cyano;

or a pharmaceutically acceptable salt, solvate, polymorph, or tautomer thereof.

3. The method according to claim 1, wherein the inhibitor of CDK8 and/or CDK19 is 7,8-dibromo-9-methyl-2-(piperazin-1-yl)-5,6-dihydro-4H-imidazo[4,5,1-ij]quinoline or a pharmaceutically acceptable salt, solvate, polymorph, or tautomer thereof.

4. The method according to claim 1, wherein the inhibitor of CDK8 and/or CDK19 has the structure of formula (XIV) or (XV):

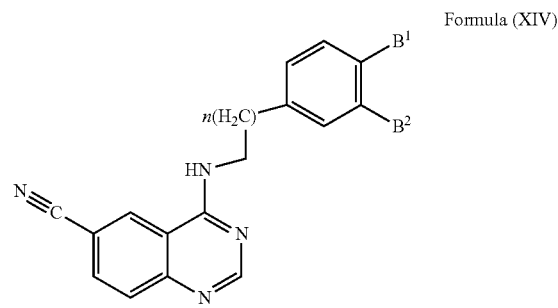

Formula (XIV)

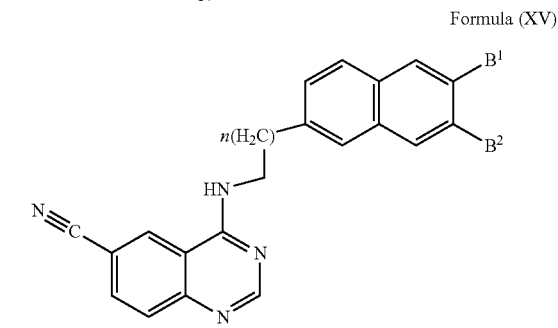

Formula (XV)

wherein B$^1$ is hydrogen when B$^2$ is a group of the formula (XVI); or wherein B$^2$ is hydrogen when B$^1$ is a group of the formula (XVI):

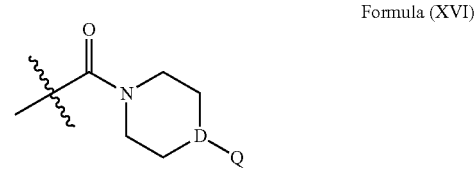

Formula (XVI)

wherein D is selected from C, O, and N; and wherein D is optionally substituted with a group Q wherein Q is selected from hydrogen, —C$_1$-C$_6$-alkyl, —C$_1$-C$_6$-alkoxy-C$_1$-C$_6$-alkyl, —C$_1$-C$_6$-alkylamine; and n is an integer 0, 1 or 2;

or a pharmaceutically acceptable salt, solvate, polymorph, or tautomer thereof.

5. The method according to claim 1, wherein the inhibitor of CDK8 and/or CDK19 has the structure of formula DBA-8 or formula DBA-9:

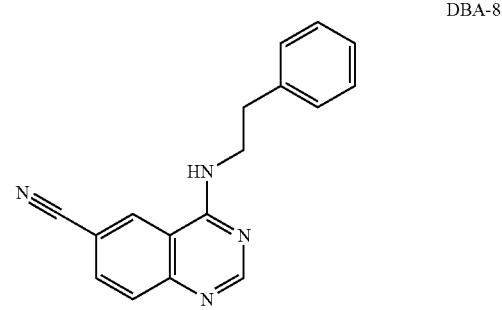

DBA-8

-continued

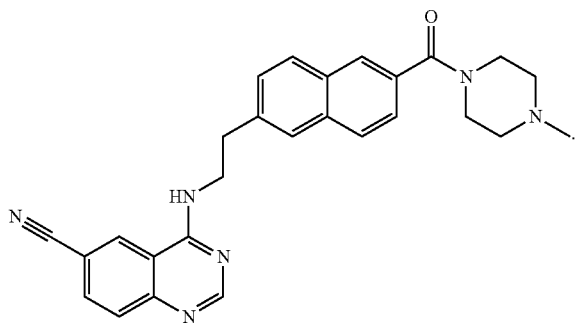

DBA-9

6. The method according to claim 1, wherein the inhibitor of CDK8 and/or CDK19 has the structure of formula (XVIII):

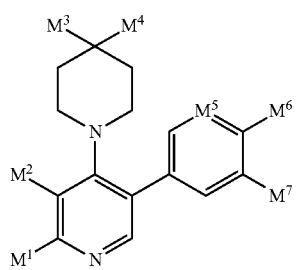

Formula (XVIII)

wherein:
$M^1$ is H or $NH_2$,
$M^2$ is LA, Hal, or CN,
$M^3$ is H, Hal, $NH_2$, LA, HO(LA)-, or NH(LA),
$M^4$ is CN, $CONH_2$, or CONH(LA)
or
$M^3$ and $M^4$ together with the C atom they are attached to, form a 5- or 6-membered non-aromatic heterocycle, having 1-3 heteroatoms, individually selected from the group consisting of O, S and N, which is substituted by 1 or 2 oxo groups, which heterocycle may further be monosubstituted by LA or OH, and which heterocycle may form a condensed ring system with a phenyl or pyridyl group,
$M^5$ is CH or N,
$M^6$ is Cyc, $CONH_2$, COO(LA) or CONH(LA),
$M^7$ is H,
or
$M^6$ and $M^7$ together with the atoms they are attached to, form a 5- or 6-membered heterocycle, having 1-3 heteroatoms, individually selected from the group consisting of O, S and N, which is, optionally, independently mono- di- or trisubstituted by oxo, OH, LA, $NH_2$, NH(LA), $N(LA)_2$) NHCOO(LA) or HO(LA)-,
Cyc is a 5- or 6-membered monocyclic, aliphatic or aromatic homo- or heterocycle having 1-3 heteroatoms, individually selected from the group consisting of O, S and N, which may be mono- or di-substituted by oxo, LA, $NH_2$, NH(LA), $N(LA)_2$, HO(LA)-, or monosubstituted by CA,
LA is an unbranched or branched alkyl, having 1, 2, 3, 4 or 5 carbon atoms, which may be saturated or partially unsaturated, wherein 1, 2 or 3 H atoms may be replaced by Hal, and/or 1 $CH_3$ group may be replaced by CN, or
1 $CH_2$ group may be replaced by —O—, —NH— or —$SO_2$—, and/or
1 CH group may be replaced by N,
CA is a cycloalkyl having 3, 4, 5 or 6 carbon atoms, or cycloalkyl alkyl having 3, 4, 5 or 6 ring carbon atoms and 1 or 2 non-ring carbon atoms, in which cycloalkyl or cycloalkyl alkyl one ring atom may be replaced by O, and which cycloalkyl or cycloalkyl alkyl may be monosubstituted by OH,
Hal is F, Cl, Br or I;
or a pharmaceutically acceptable salt, solvate, polymorph, or tautomer thereof.

7. The method according to claim 1, wherein the inhibitor of CDK8 and/or CDK19 has the structure of formula DBA-11:

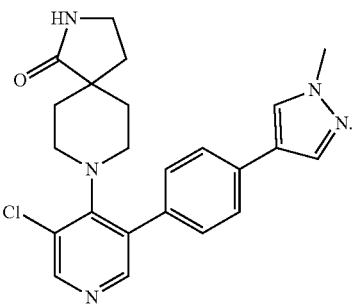

DBA-11

8. The method according to claim 1, wherein the inhibitor of CDK8 and/or CDK19 has the structure of formula DBA-12:

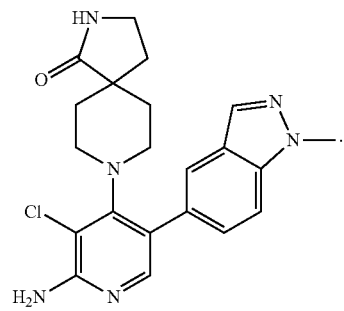

DBA-12

9. The method according to claim 1, wherein the inhibitor of CDK8 and/or CDK19 has the structure of formula (I):

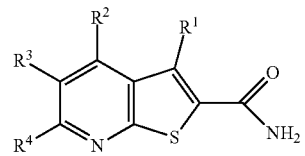

Formula (I)

wherein:
$R^1$ is selected from the group consisting of a hydrogen atom, $C_1$-$C_6$ alkyl, —$NH_2$, and alkyl-amine,
$R^2$ is selected from the group consisting of a hydrogen atom, —$N(CH_3)_2$, —$NH_2$, methyl, trifluoromethyl, —CH$_2$OCH$_3$, -PhOCH$_3$, -PhCH$_3$, -PhCl, and a group of any one of the formulas (II), (III), (IV) and (V):

Formula (II)

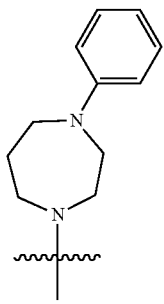

Formula (III)

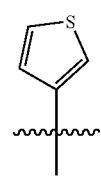

Formula (IV)

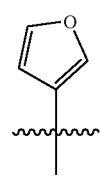

Formula (V)

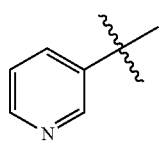

R$^3$ is selected from the group consisting of a hydrogen atom, methyl, acetyl, phenyl, cyclopropyl, and a group of the formula (V):

Formula (V)

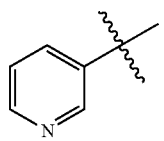

R$^4$ is selected from the group consisting of a hydrogen atom, methyl, ethyl, cyclopropyl, C$_1$-C$_6$ alkyl, acetyl, phenyl, trifluoromethyl, —CH$_2$CH(CH$_3$)$_2$, -PhCl, -PhCH$_3$, and a group of the formulas (III) or (VII):

Formula (III)

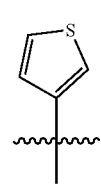

-continued

Formula (VII)

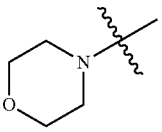

or wherein R$^4$ is an oxygen atom double bonded to the carbon atom of the thienopyridine ring thus forming a structure of formula (VI):

Formula (VI)

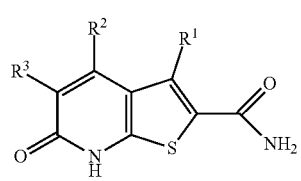

or wherein R$^2$ and R$^3$ are joined to form a 6-membered cyclic structure of the formula (VIII):

Formula (VIII)

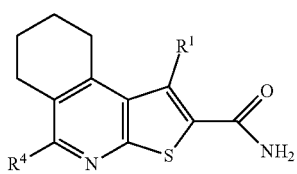

or wherein R$^3$ and R$^4$ are joined to form a 5-, 6- or 7-membered cyclic structure of any one of the formulas (IX), (X), (XI) or (XII):

Formula (IX)

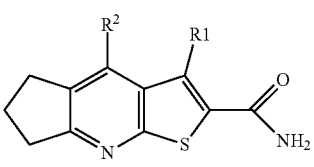

Formula (X)

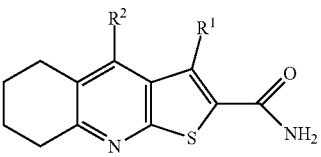

Formula (XI)

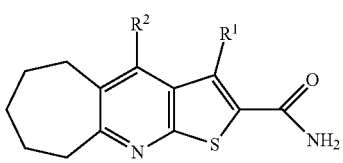

Formula (XII)

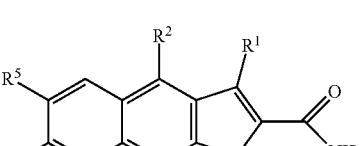

wherein $R^5$ and $R^6$ optionally and individually are —$OCH_3$;

or a pharmaceutically acceptable salt, solvate, polymorph, or tautomer thereof.

10. The method according to claim 1, wherein the inhibitor of CDK8 and/or CDK19 has the structure of formula (I):

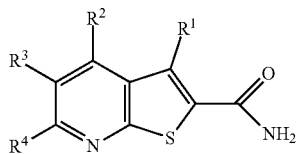

Formula (I)

wherein:

$R^1$ is —$NH_2$;

$R^2$ represents $R^aS$—, $R^aO$—, $R^aNH$—, $R^a(R^b)N$— or a group of formula (XIII):

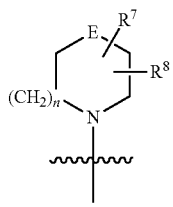

Formula (XIII)

wherein $R^a$ and $R^b$ are the same or different and independently represent a $C_1$-$C_6$ alkyl group which may be substituted with one or more groups selected from Substituent Group α and Substituent Group γ; a $C_3$-$C_8$ cycloalkyl group which may be substituted with one or more groups selected from Substituent Group α, Substituent Group β and Substituent Group γ; a 5- to 7-membered heterocyclyl group which may be substituted with one or more groups selected from Substituent Group α, Substituent Group β and Substituent Group γ and which contains 1 to 3 sulfur, oxygen and/or nitrogen atoms; a $C_6$-$C_{10}$ aryl group which may be substituted with one or more groups selected from Substituent Group α, Substituent Group β and Substituent Group γ; or a 5- to 7-membered heteroaryl group which may be substituted with one or more groups selected from Substituent Group α, Substituent Group β and Substituent Group γ and which contains 1 to 3 sulfur, oxygen and/or nitrogen atoms, $R^7$ and $R^8$ are the same or different and independently represent a hydrogen atom; a group selected from Substituent Group α, Substituent Group β and Substituent Group γ; a $C_1$-$C_6$ alkyl group substituted with one or more groups selected from Substituent Group γ; or a $C_1$-$C_6$ alkoxy group substituted with one or more groups selected from Substituent Group γ, or when $R^7$ and $R^8$ are bonded to adjacent carbon atoms, $R^7$ and $R^8$ together with the carbon atoms to which they are bonded may form a $C_3$-$C_8$ cycloalkyl group which may be substituted with one or more groups selected from Substituent Group α, Substituent Group β and Substituent Group γ; a 5- to 7-membered heterocyclyl group which may be substituted with one or more groups selected from Substituent Group α, Substituent Group β and Substituent Group γ and which contains 1 to 3 sulfur, oxygen and/or nitrogen atoms; a $C_6$-$C_{10}$ aryl group which may be substituted with one or more groups selected from Substituent Group α, Substituent Group β and Substituent Group γ; or a 5- to 7-membered heteroaryl group which may be substituted with one or more groups selected from Substituent Group α, Substituent Group β and Substituent Group γ and which contains 1 to 3 sulfur, oxygen and/or nitrogen atoms, E represents a single bond; a double bond; an oxygen atom; a sulfur atom; sulfinyl; sulfonyl, or a group having the formula $R_9N<$;

$R_9$ represents a hydrogen atom; a $C_1$-$C_6$ alkyl group which may be substituted with one or more groups selected from Substituent Group α and Substituent Group γ; a $C_2$-$C_6$ alkenyl group which may be substituted with one or more groups selected from Substituent Group α and Substituent Group γ; a $C_3$-$C_8$ cycloalkyl group which may be substituted with one or more groups selected from Substituent Group α, Substituent Group β and Substituent Group γ; a 5- to 7-membered heterocyclyl group which may be substituted with one or more groups selected from Substituent Group α, Substituent Group β and Substituent Group γ and which contains 1 to 3 sulfur, oxygen and/or nitrogen atoms; a $C_6$-$C_{10}$ aryl group which may be substituted with one or more groups selected from Substituent Group α, Substituent Group β and Substituent Group γ; a 5- to 7-membered heteroaryl group which may be substituted with one or more groups selected from Substituent Group α, Substituent Group β and Substituent Group γ and which contains 1 to 3 sulfur, oxygen and/or nitrogen atoms; a formyl group; a $C_2$-$C_7$ alkylcarbonyl group which may be substituted with one or more groups selected from Substituent Group α and Substituent Group γ; a 5- to 7-membered heterocyclylcarbonyl group which may be substituted with one or more groups selected from Substituent Group α, Substituent Group β and Substituent Group γ and which contains 1 to 3 sulfur, oxygen and/or nitrogen atoms; a $C_7$-$C_{11}$ arylcarbonyl group which may be substituted with one or more groups selected from Substituent Group α, Substituent Group β and Substituent Group γ; a 5- to 7-membered heteroarylcarbonyl group which may be substituted with one or more groups selected from Substituent Group α, Substituent Group β and Substituent Group γ and which contains 1 to 3 sulfur, oxygen and/or nitrogen atoms; a $C_1$-$C_6$ alkylsulfonyl group which may be substituted with one or more groups selected from Substituent Group α and Substituent Group γ; a $C_6$-$C_{10}$ arylsulfonyl group which may be substituted with one or more groups selected from Substituent Group α, Substituent Group β and Substituent Group γ; a 5- to 7-membered heteroarylsulfonyl group which may be substituted with one or more groups selected from Substituent Group α, Substituent Group β and Substituent Group γ and which contains 1 to 3 sulfur, oxygen and/or nitrogen atoms; a $C_2$-$C_7$ alkoxycarbonyl group which may be substituted with one or more groups selected from Substituent Group α and Substituent Group γ; a $C_7$-$C_{11}$ aryloxycarbonyl group which may be substituted with one or more groups selected from Substituent Group α, Substituent Group β and Substituent Group γ; or a group having the formula $R^c(R^d)N$—CO— (wherein $R^c$ and $R^d$ are the same or different and independently represent a hydrogen atom or a $C_1$-$C_6$ alkyl group which may be substituted with one or more groups selected from Substituent Group α and Substituent Group γ), n represents an integer of 1 to 4, Substituent Group α represents the group consisting of a halogen atom; a nitro group; a cyano group; a hydroxy group; a group having the formula $R^{10}$—CO—, the formula $R^e(R^f)N$—, the formula $R^e(R^f)N$—CO— or the formula $R^e(R^f)N$—$SO_2$— (wherein $R^{10}$ represents a hydrogen atom, a $C_1$-$C_6$ alkyl group, a $C_1$-$C_6$ halogenated alkyl group, a $C_3$-$C_8$ cycloalkyl group, a hydroxy group, a $C_1$-$C_6$ alkoxy group, a $C_6$-$C_{10}$ aryl group or a $C_6$-$C_{10}$ aryloxy group and $R^e$ and $R^f$ are the same or different and independently represent a hydrogen atom; a $C_1$-$C_6$ alkyl group; a $C_1$-$C_6$ alkoxy group; a $C_6$-$C_{10}$ aryl group; a 5- to 7-membered heteroaryl group which contains 1 to 3 sulfur, oxygen and/or nitrogen atoms; a formyl group; a $C_2$-$C_7$ alkylcarbonyl group; a $C_2$-$C_7$ alkoxycarbonyl group; a $C_7$-$C_{11}$ arylcarbonyl group; a 5- to 7-membered heteroarylcarbonyl group which contains 1 to 3 sulfur, oxygen and/or nitrogen atoms; a $C_1$-$C_6$ alkylsulfonyl group; a $C_6$-$C_{10}$ arylsulfonyl group; or a 5- to 7-membered heteroarylsulfonyl group which contains 1 to 3 sulfur, oxygen and/or nitrogen atoms, or alternatively $R^e$ and $R^f$ together with the nitrogen atom to which they are bonded form a 4- to 7-membered heterocyclyl group which contains 1 to 3 sulfur, oxygen and/or nitrogen atoms (wherein the heterocyclyl group may have 1 or 2 substituent groups selected from a hydroxy group and a methyl group)); a hydroxyimino group; a $C_1$-$C_6$ alkoxyimino group; a $C_1$-$C_6$ alkoxy group; a $C_3$-$C_8$ cycloalkyloxy group; a $C_1$-$C_6$ halogenated alkoxy group; a $C_1$-$C_6$ alkylthio group; a $C_1$-$C_6$ alkylsulfinyl group; and a $C_1$-$C_6$ alkylsulfonyl group, Substituent Group β represents the group consisting of a $C_1$-$C_6$ alkyl group which may be substituted with one or more groups selected from Substituent Group α; and a $C_1$-$C_6$ alkyl group substituted with a 5- to 7-membered heterocyclyl group which may be substituted with one or more groups selected from Substituent Group α, and a $C_1$-$C_6$ alkyl group and which contains 1 to 3 sulfur, oxygen and/or nitrogen atoms, and Substituent Group γ represents the group consisting of a $C_1$-$C_6$ alkoxy group substituted with one or more groups selected from Substituent Group α; a $C_1$-$C_6$ alkylthio group substituted with one or more groups selected from Substituent Group α; a $C_3$-$C_8$ cycloalkyl group which may be substituted with one or more groups selected from Substituent Group α and Substituent Group β; a 5- to 7-membered heterocyclyl group which may be substituted with one or more groups selected from Substituent Group α and Substituent Group β and which contains 1 to 3 sulfur, oxygen and/or nitrogen atoms; a $C_6$-$C_{10}$ aryl group which may be substituted with one or more groups selected from Substituent Group α and Substituent Group β; a 5- to 7-membered heteroaryl group which may be substituted with one or more groups selected from Substituent Group α and Substituent Group β and which contains 1 to 3 sulfur, oxygen and/or nitrogen atoms; a $C_3$-$C_8$ cycloalkyloxy group which may be substituted with one or more groups selected from Substituent Group α and Substituent Group β a 5- to 7-membered heterocyclyloxy group which may be substituted with one or more groups selected from Substituent Group α and Substituent Group β and which contains 1 to 3 sulfur, oxygen and/or nitrogen atoms; a $C_6$-$C_{10}$ aryloxy group which may be substituted with one or more groups selected from Substituent Group α and Substituent Group β; a 5- to 7-membered heteroaryloxy group which may be substituted with one or more groups selected from Substituent Group α and Substituent Group β and which contains 1 to 3 sulfur, oxygen and/or nitrogen atoms; and a $C_6$-$C_{10}$ aryl-$C_1$-$C_6$ alkoxy group in which the aryl moiety may be substituted with one or more groups selected from Substituent Group α and Substituent Group β or a pharmacologically acceptable salt thereof;

$R^3$ is a hydrogen atom; and $R^4$ is selected from the group consisting of a hydrogen atom, a cyclopropyl group or a $C_1$-$C_6$ alkyl group;

or a pharmaceutically acceptable salt, solvate, polymorph, or tautomer thereof.

11. The method according to claim 1, wherein the inhibitor of CDK8 and/or CDK19 is selected from the group consisting of:

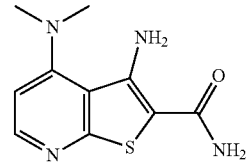

DBA-1

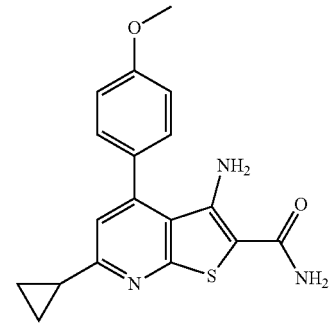

DBA-2

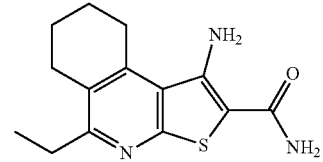

DBA-3

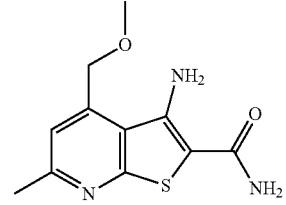

DBA-4

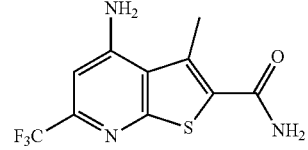

DBA-5

DBA-6

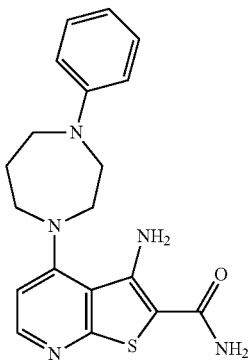

DBA-7

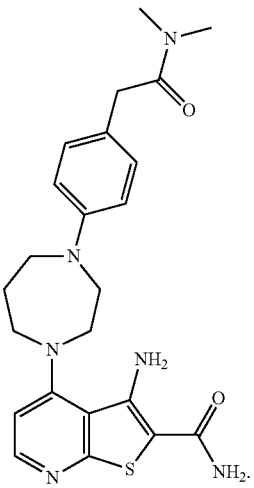

12. The method according to claim 1, wherein the ribosomopathy and/or the disease characterized by reduced number of hematopoietic stem cells and/or progenitor cells are selected from the group consisting of Diamond-Blackfan anemia, Dyskeratosis congenita, Shwachman-Diamond syndrome, 5q-myelodysplastic syndrome, Treacher Collins syndrome, Cartilage-hair hypoplasia, North American Indian childhood cirrhosis, Isolated congenital asplenia, Bowen-Conradi syndrome, Turners syndrome, and Fanconi's anemia.

13. The method according to claim 1, wherein the ribosomopathy is an anemia.

14. The method according to claim 1, wherein the ribosomopathy is an immunodeficiency growth retardation.

15. The method according to claim 1, wherein the ribosomopathy is Diamond Blackfan anemia.

16. The method according to claim 1, wherein said bone anabolic disorder is osteopathy or osteoarthritis.

17. A method of treating a clinical condition in an individual in need thereof, wherein the clinical condition is selected from the group consisting of a bone anabolic disorder, a ribosomopathy, and/or a disease characterized by reduced number of hematopoietic stem cells and/or progenitor cells, wherein the method comprises administering a therapeutically effective amount of a compound selected from the group consisting of:

a) a compound having the structure of formula (XVII):

Formula (XVII)

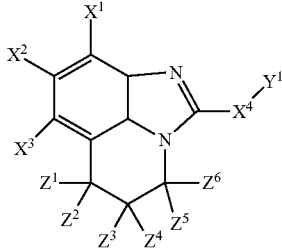

wherein $X^1$, $X^2$ and $X^3$ are each independently selected from the group consisting of H, F, Cl, Br, I, —$OT^1$, —$N(T^2)(T^3)$, —$NHC(=O)T^4$, nitro, cyano, cyclopropyl and —$C_1$-$C_3$ alkyl, with the proviso that at least two substituents selected from $X^1$, $X^2$ and $X^3$ are each independently selected from the group consisting of F, Cl, Br and I;

$Z^1$ and $Z^2$ are each independently selected from the group consisting of H, —$C_1$-$C_6$ alkyl, —$OT^1$ and —$N(T^2)(T^3)$;

$Z^3$ and $Z^4$ are either taken together to form an oxo group at the carbon atom to which they are attached; or $Z^3$ and $Z^4$ are each independently selected from the group consisting of H, —$C_1$-$C_6$ alkyl, —$OT^1$ and —$N(T^2)(T^3)$;

$Z^5$ and $Z^6$ are either taken together to form an oxo group at the carbon atom to which they are attached; or $Z^5$ and $Z^6$ are each independently selected from the group consisting of H, —$C_1$-$C_6$ alkyl, —$OT^1$ and —$N(T^2)(T^3)$, $X^4$ is either absent or selected from the group consisting of —$NR^{12}$—, —$N(R^{12})(CH_2)$—, —$C(=O)NH$— and —$C(=O)$—; wherein $R^{32}$ is selected from H and —$C_1$-$C_6$ alkyl;

$Y^1$ is selected from the group consisting of H, —$C_1$-$C_6$ alkyl and a 4- to 7-membered saturated or unsaturated aromatic carbocycle or heterocycle, with the proviso that the point of attachment on said heterocycle is carbon if $X^4$ is $NR^{12}$— or —$C(=O)NH$—, wherein said —$C_1$-$C_6$ alkyl is optionally substituted with one or more substituents independently selected from —$OT^1$, —$ST^1$, —$N(T^2)(T^3)$ and a 5- to 6-membered saturated heterocycle, and wherein said 4- to 7-membered saturated or unsaturated aromatic carbocycle or heterocycle is optionally substituted with one or more substituents independently selected from F, Cl, Br, I, —$C(=O)H$, —$OT^1$, —$N(T^2)(T^3)$, —$C(=O)N(T^2)(T^3)$, —$C(=O)$ $O1^{-4}$, —$ST^1$ and —$C_1$-$C_3$ alkyl, wherein said —$C_1$-$C_3$ alkyl is optionally substituted with one or more substituents independently selected from —$OT^1$ and —$N(T^2)(T^3)$;

$T^1$, $T^2$ and $T^3$ are each independently selected from H and —$C_1$-$C_6$ alkyl optionally substituted with one or more substituents independently selected from —$N(T^5)(T^6)$, —$OT^7$, —$ST^7$, nitro, cyano, —$C(=O)OT^7$, —$C(=O)N(T^5)(T^6)$, —$OC(=O)N(T^5)(T^6)$, —$S(=O)_2T^7$, —$S(=O)_2OT^8$ and —$S(=O)_2N(T^5)(T^6)$;

$T^4$ is —$C_1$-$C_6$ alkyl optionally substituted with one or more substituents independently selected from —$N(T^5)(T^6)$, —$OT^7$, —$ST^7$, nitro, cyano, —$C(=O)OT^7$, —$C(=O)N(T^5)(T^6)$, —$OC(=O)N(T^5)(T^6)$, —$S(=O)_2T^8$, —$S(=O)_2OT^7$ and —$S(=O)_2N(T^5)(T^6)$;

$T^5$, $T^6$ and $T^7$ are each independently selected from H and —$C_1$-$C_6$ alkyl optionally substituted with one or more substituents independently selected from amino, hydroxyl, thiol, nitro and cyano; and T⁸ is selected from —C₁-C₆ alkyl optionally substituted with one or more substituents independently selected from amino, hydroxyl, thiol, nitro and cyano;

b) a compound having the structure of formula (XIV) or (XV):

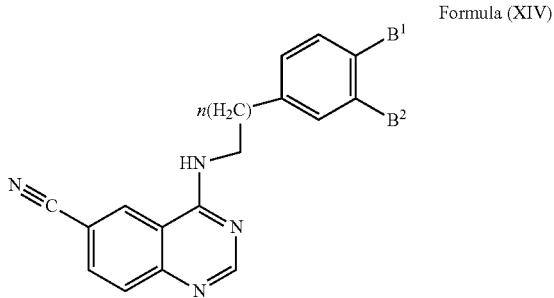

Formula (XIV)

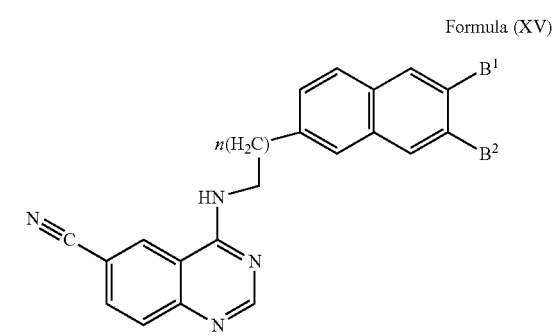

Formula (XV)

wherein B¹ is hydrogen when B² is a group of the formula (XVI); or wherein B² is hydrogen when B¹ is a group of the formula (XVI):

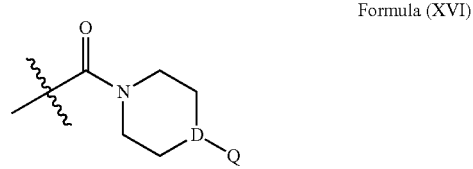

Formula (XVI)

wherein D is selected from C, O, and N; and wherein D is optionally substituted with a group Q wherein Q is selected from hydrogen, —C₁-C₆-alkyl, —C₁-C₆-alkoxy-C₁-C₆-alkyl, —C₁-C₆-alkylamine; and n is an integer 0, 1 or 2;

c) a compound having the structure of formula (XVIII):

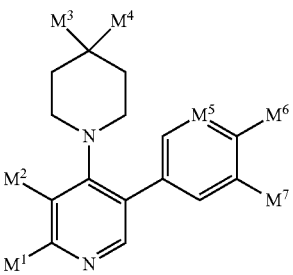

Formula (XVIII)

wherein:

M¹ is H or NH₂,

M² is LA, Hal, or CN,

M³ is H, Hal, NH₂, LA, HO(LA)-, or NH(LA),

M⁴ is CN, CONH₂, or CONH(LA)

or

M³ and M⁴ together with the C atom they are attached to, form a 5- or 6-membered non-aromatic heterocycle, having 1-3 heteroatoms, individually selected from the group consisting of O, S and N, which is substituted by 1 or 2 oxo groups, which heterocycle may further be monosubstituted by LA or OH, and which heterocycle may form a condensed ring system with a phenyl or pyridyl group, M⁵ is CH or N, M⁶ is Cyc, CONH₂, COO(LA) or CONH(LA), M⁷ is H, or M⁶ and M⁷ together with the atoms they are attached to, form a 5- or 6-membered heterocycle, having 1-3 heteroatoms, individually selected from the group consisting of O, S and N, which is, optionally, independently mono- di- or trisubstituted by oxo, OH, LA, NH₂, NH(LA), N(LA)₂) NHCOO(LA) or HO(LA)-, Cyc is a 5- or 6-membered monocyclic, aliphatic or aromatic homo- or heterocycle having 1-3 heteroatoms, individually selected from the group consisting of O, S and N, which may be mono- or di-substituted by oxo, LA, NH₂, NH(LA), N(LA)₂, HO(LA)-, or monosubstituted by CA, LA is an unbranched or branched alkyl, having 1, 2, 3, 4 or 5 carbon atoms, which may be saturated or partially unsaturated, wherein 1, 2 or 3 H atoms may be replaced by Hal, and/or 1 CH₃ group may be replaced by CN, or 1 CH₂ group may be replaced by —O—, —NH— or —SO₂—, and/or 1 CH group may be replaced by N, CA is a cycloalkyl having 3, 4, 5 or 6 carbon atoms, or cycloalkyl alkyl having 3, 4, 5 or 6 ring carbon atoms and 1 or 2 non-ring carbon atoms, in which cycloalkyl or cycloalkyl alkyl one ring atom may be replaced by O, and which cycloalkyl or cycloalkyl alkyl may be monosubstituted by OH, Hal is F, Cl, Br or I;
and
d) a compound having the formula (I):

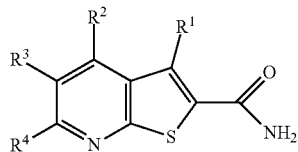

Formula (I)

wherein:

IV is selected from the group consisting of a hydrogen atom, $C_1$-$C_6$ alkyl, —$NH_2$, and alkyl-amine, $R^2$ is selected from the group consisting of a hydrogen atom, —$N(CH_3)_2$, —$NH_2$, methyl, trifluoromethyl, —$CH_2OCH_3$, -$PhOCH_3$, -$PhCH_3$, -PhCl, and a group of any one of the formulas (II), (III), (IV) and (V):

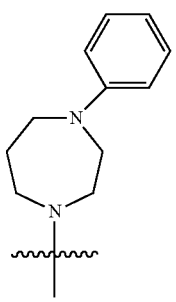

Formula (II)

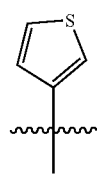

Formula (III)

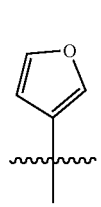

Formula (IV)

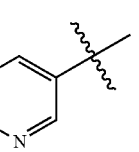

Formula (V)

$R^3$ is selected from the group consisting of a hydrogen atom, methyl, acetyl, phenyl, cyclopropyl, and a group of the formula (V):

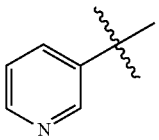

Formula (V)

$R^4$ is selected from the group consisting of a hydrogen atom, methyl, ethyl, cyclopropyl, $C_1$-$C_6$ alkyl, acetyl, phenyl, trifluoromethyl, —$CH_2CH(CH_3)_2$, -PhCl, -$PhCH_3$, and a group of the formulas (III) or (VII):

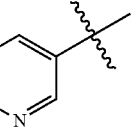

Formula (III)

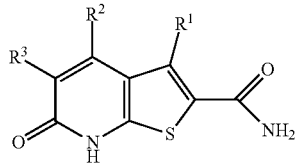

Formula (VII)

or wherein $R^4$ is an oxygen atom double bonded to the carbon atom of the thienopyridine ring thus forming a structure of formula (VI):

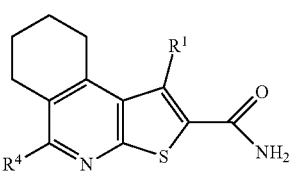

Formula (VI)

or wherein $R^2$ and $R^3$ are joined to form a 6-membered cyclic structure of the formula (VIII):

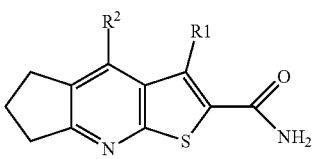

Formula (VIII)

or wherein $R^3$ and $R^4$ are joined to form a 5-, 6- or 7-membered cyclic structure of any one of the formulas (IX), (X), (XI) or (XII):

Formula (IX)

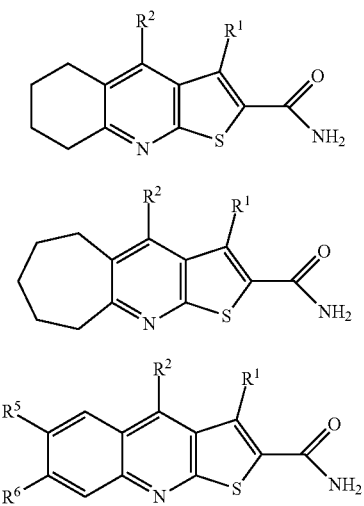

Formula (X)

Formula (XI)

Formula (XII)

wherein $R^5$ and $R^6$ optionally and individually are —$OCH_3$;

or a pharmaceutically acceptable salt, solvate, polymorph, or tautomer thereof.

18. The method according to claim 17, wherein the ribosomopathy is selected from the group consisting of Diamond-Blackfan anemia, Dyskeratosis congenita, Shwachman-Diamond syndrome, 5q-myelodysplastic syndrome, Treacher Collins syndrome, Cartilage-hair hypoplasia, North American Indian childhood cirrhosis, Isolated congenital asplenia, Bowen-Conradi syndrome, Turners syndrome, and Fanconi's anemia.

19. The method according to claim 17, wherein the ribosomopathy is Diamond Blackfan anemia.

20. The method according to claim 17, wherein said bone anabolic disorder is osteopathy or osteoarthritis.

* * * * *

UNITED STATES PATENT AND TRADEMARK OFFICE
CERTIFICATE OF CORRECTION

PATENT NO. : 11,471,446 B2
APPLICATION NO. : 15/772633
DATED : October 18, 2022
INVENTOR(S) : J. Flygare et al.

Page 1 of 1

It is certified that error appears in the above-identified patent and that said Letters Patent is hereby corrected as shown below:

In the Claims

In Claim 6, Column 35, Line 57, "$N(LA)_2$)" should read -- $N(LA)_2$, --.

In Claim 10, Column 41, Line 63, "Substituent Group $\beta$" should read -- Substituent Group $\beta$; --.

In Claim 17, Column 46, Line 44, "$N(LA)_2$)" should read -- $N(LA)_2$, --.

In Claim 17, Column 47, in the beginning of Line 16, "IV" should read -- $R^1$ --.

Signed and Sealed this
Seventeenth Day of October, 2023

Katherine Kelly Vidal
*Director of the United States Patent and Trademark Office*